(12) United States Patent
Vulto et al.

(10) Patent No.: US 9,771,553 B2
(45) Date of Patent: Sep. 26, 2017

(54) APPARATUS FOR AND METHODS OF PROCESSING LIQUIDS OR LIQUID-BASED SUBSTANCES

(75) Inventors: Paul Vulto, Leiden (NL); Sebastiaan Johannes Trietsch, Leiden (NL); Heiko Jan van der Linden, Leiden (NL); Thomas Hankemeier, Leiden (NL)

(73) Assignee: UNIVERSITEIT LEIDEN, Leiden (NL)

( * ) Notice: Subject to any disclaimer, the term of this patent is extended or adjusted under 35 U.S.C. 154(b) by 0 days.

(21) Appl. No.: 14/003,606

(22) PCT Filed: Mar. 8, 2012

(86) PCT No.: PCT/EP2012/054053
§ 371 (c)(1),
(2), (4) Date: Sep. 6, 2013

(87) PCT Pub. No.: WO2012/120101
PCT Pub. Date: Sep. 13, 2012

(65) Prior Publication Data
US 2013/0340883 A1 Dec. 26, 2013

(30) Foreign Application Priority Data
Mar. 8, 2011 (GB) .................................. 1103917.9

(51) Int. Cl.
*B01L 3/00* (2006.01)
*C12M 1/00* (2006.01)
(Continued)

(52) U.S. Cl.
CPC ......... *C12M 27/18* (2013.01); *B01F 13/0083* (2013.01); *B01L 3/502746* (2013.01);
(Continued)

(58) Field of Classification Search
CPC ....... B01L 3/502746; B01L 2400/0688; B01L 2400/086
(Continued)

(56) References Cited

U.S. PATENT DOCUMENTS 6,180,062 B1 1/2001 Naka et al.
6,296,020 B1 * 10/2001 McNeely et al. ............. 137/806
(Continued)

FOREIGN PATENT DOCUMENTS

| EP | 2213364 | 8/2010 |
| WO | 2008/083526 | 7/2008 |
| WO | 2010/086179 A2 | 8/2010 |

OTHER PUBLICATIONS

Vulto et al., Journal of Micromechanics & Microengineering, 16(9):1847-1853 (2006). "Selective sample recovery of DEP-separated cells and particles by phaseguide-controlled laminar flow; selective sample recovery of DEP-separated particles."
(Continued)

*Primary Examiner* — Sean E Conley
*Assistant Examiner* — Benjamin R Whatley
(74) *Attorney, Agent, or Firm* — Nixon Peabody LLP

(57) ABSTRACT

Apparatus for processing liquids or liquid-based substances includes a plurality of volumes at least two of which are defined at least in part by one or more phaseguides inside the volume and/or in a conduit connected thereto for controlling aliquoting of one or more liquids or liquid-based substances inside the volume. Each volume has an upstream and downstream side with respect to meniscus advancement direction via which it may be filled with or emptied of one or more liquids or liquid-based substances. The apparatus also includes at least one common upstream-side conduit connected to supply a liquid or liquid-based substance via a plurality of the inlet or extraction conduits, a plurality of the
(Continued)

phaseguides exhibiting a predetermined level of stability and one or more of the phaseguides exhibiting a predetermined different stability compared with the stability of at least one of the other phaseguides whereby to control the preference order in which the volumes fill and/or empty. The stability is determined by the value and radius of an acute angle along a said phaseguide at the downstream side of the phaseguide.

14 Claims, 23 Drawing Sheets

(51) Int. Cl.
*B01F 13/00* (2006.01)
*C12M 3/06* (2006.01)
*C12M 1/42* (2006.01)

(52) U.S. Cl.
CPC ............... *B01L 3/56* (2013.01); *C12M 23/16* (2013.01); *C12M 23/34* (2013.01); *C12M 29/10* (2013.01); *C12M 35/08* (2013.01); *B01L 2200/0605* (2013.01); *B01L 2200/0621* (2013.01); *B01L 2200/0684* (2013.01); *B01L 2300/087* (2013.01); *B01L 2300/089* (2013.01); *B01L 2300/0816* (2013.01); *B01L 2300/0851* (2013.01); *B01L 2300/0864* (2013.01); *B01L 2300/0867* (2013.01); *B01L 2300/161* (2013.01); *B01L 2400/0406* (2013.01); *B01L 2400/0688* (2013.01); *B01L 2400/086* (2013.01); *B01L 2400/088* (2013.01); *Y10T 137/0318* (2015.04)

(58) Field of Classification Search
USPC ................... 422/504, 537; 435/286.5, 287.3; 137/825, 834
See application file for complete search history.

(56) References Cited

U.S. PATENT DOCUMENTS

| | | | |
|---|---|---|---|
| 6,601,613 B2 | 8/2003 | McNeely | |
| 6,637,463 B1 | 10/2003 | Lei | |
| 6,843,262 B2* | 1/2005 | Ismagilov | ............... F15C 1/146 137/137 |
| 2007/0280856 A1 | 12/2007 | Ulmanella et al. | |
| 2010/0024888 A1* | 2/2010 | Guan | ........................ B01F 5/04 137/3 |
| 2010/0120077 A1* | 5/2010 | Daridon | ............ B01L 3/502761 435/29 |
| 2010/0252118 A1* | 10/2010 | Fraden | .............. B01L 3/502746 137/2 |
| 2010/0261290 A1* | 10/2010 | Nakajima | ......... B01L 3/502784 436/174 |
| 2012/0097272 A1* | 4/2012 | Vulto | ................ B01L 3/502746 137/561 R |

OTHER PUBLICATIONS

Vulto et al., "Phaseguides: a paradigm shift in microfluidic priming and emptying", Lab Chip 11(9):1596-1602 (2011).

Yildirim et al., "Phaseguides as tunable passive microvalves for liquid routing in complex microfluidic networks", Lap Chip 14(17):3334-3340 (2014).

* cited by examiner

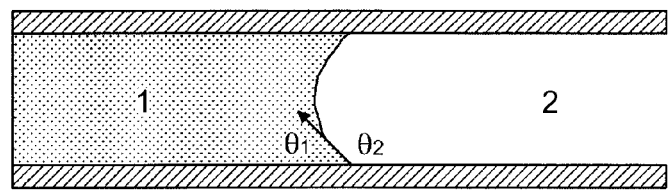
Figure 1a
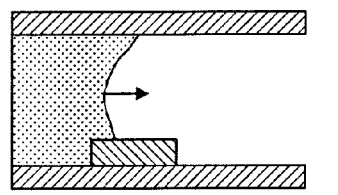 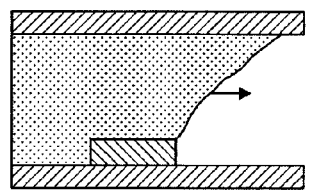 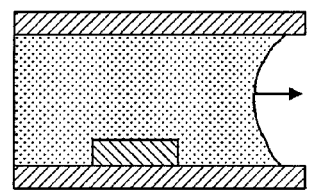
Figure 1b        Figure 1c        Figure 1d
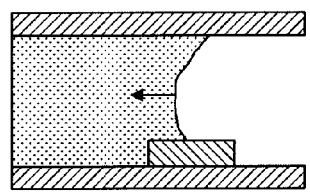 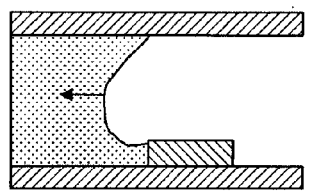 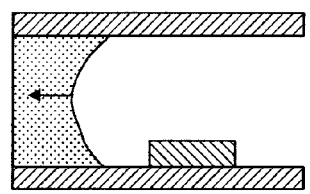
Figure 1e        Figure 1f        Figure 1g

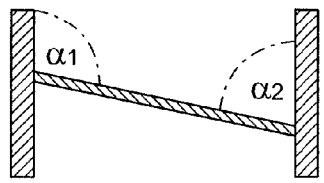 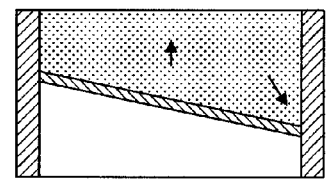 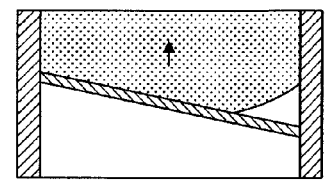
Figure 3a  Figure 3b  Figure 3c
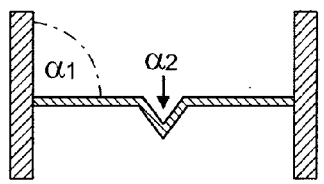 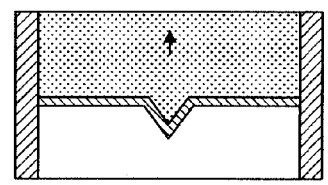 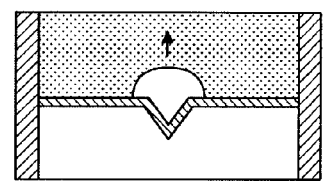
Figure 3d  Figure 3e  Figure 3f
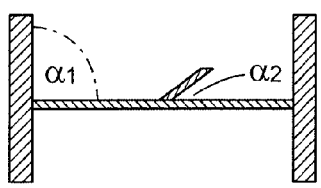 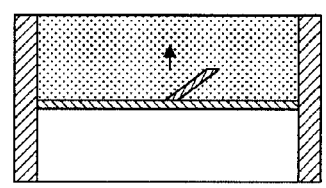 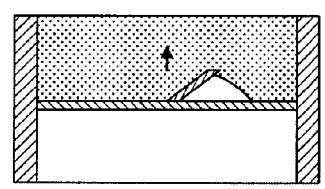
Figure 3g  Figure 3h  Figure 3i

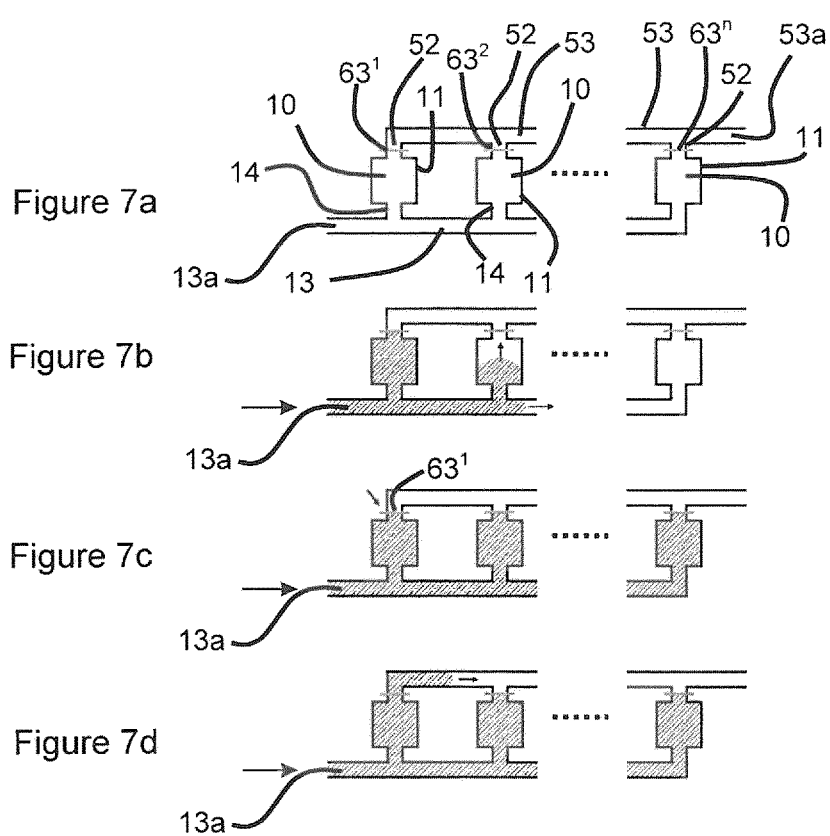

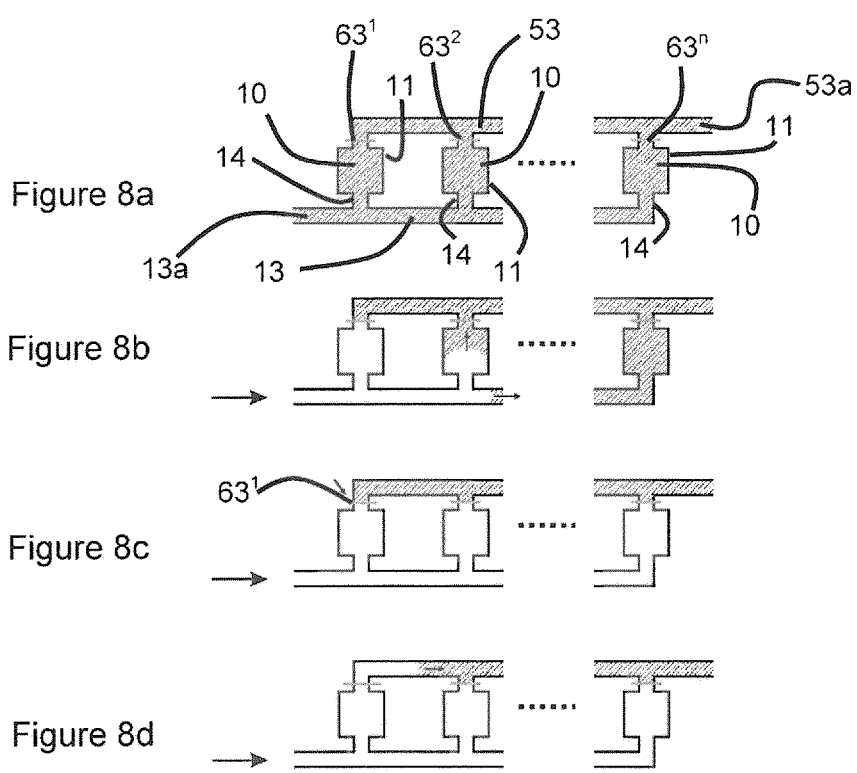

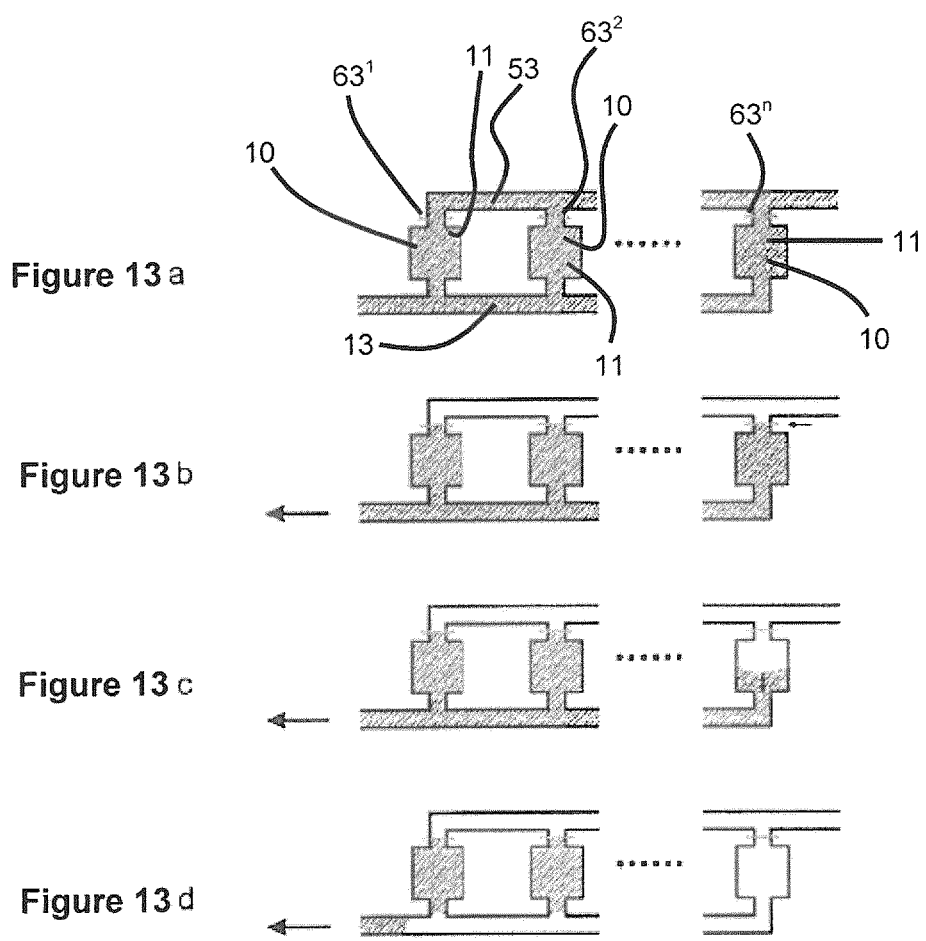

APPARATUS FOR AND METHODS OF PROCESSING LIQUIDS OR LIQUID-BASED SUBSTANCES

CROSS REFERENCE TO RELATED APPLICATIONS

This application is a 35 U.S.C. §371 National Phase Entry Application of International Application No. PCT/EP2012/054053 filed Mar. 8, 2012, which designates the United States, and which claims benefit of Great Britain Application No. 1103917.9 filed Mar. 8, 2011, the contents of each of which are incorporated herein by reference in their entireties.

This invention relates to apparatuses for and methods of processing liquids or liquid-based substances. In particular the invention relates to such apparatuses and methods when based on microfluidic volumes containing phaseguides.

A phaseguide is a structure, in a volume that is to be filled with or emptied of a liquid, that limits the ability of the meniscus of a body of liquid to advance or recede in the volume, thereby defining an interface between the liquid and another substance (i.e. another liquid, or a gas) that is of predetermined shape.

Phaseguides may be constructed in a variety of ways. One technique involves constructing a sharp edge. Advancement over such a sharp edge requires a change of the principal radii of a fluid-fluid meniscus, leading to a higher pressure drop over the meniscus thus representing a pressure barrier. This concept is also known as "meniscus pinning."

A typical phaseguide is therefore a three-dimensional structure that protrudes into the liquid along the complete length of the meniscus. Pinning of the meniscus on the resulting, elongate protrusion requires such additional energy for the liquid meniscus to cross it that the liquid is confined unless additional energy is applied to the body of liquid.

Another typical phaseguide is a ridge protruding into the bulk material. In this case pinning occurs before the phaseguide.

In addition, the phaseguide may include a usually deliberate location of weakness at which the energy required to cross the phaseguide is lower. At such a location the liquid may, if the phaseguide is properly designed, cross the phaseguide. This deliberate location of weakness also defines the "stability" of a phaseguide, which determines the order or priority of phaseguide overflow when a bulk liquid faces multiple phaseguides simultaneously during meniscus advancement or recession.

A particularly versatile phaseguide is created when the substrate facing the phaseguide is more hydrophilic than the phaseguide itself. Such an implementation leads to stretching of the meniscus and increases the effect that angles and their radii have on the stability of a phaseguide.

Thus the phaseguides may, depending on their precise design, either confine a liquid completely; or may permit its advancement or recession only at a preferred location so that the liquid follows a chosen path, fills or empties a particular space in the volume, or adopts a particular shape.

Phaseguides may instead of being constructed as protruding barriers be defined by areas on an internal surface of a volume that are of differing degrees of wettability. Again such areas may cause a requirement for the input of energy in order to encourage a liquid meniscus to advance across them.

Numerous designs of phaseguide structure are disclosed in WO2010/086179 A2. An understanding of this publication is desirable from the standpoint of explaining the invention, so the entire content of WO2010/086179 A2 is incorporated herein by reference.

U.S. Pat. No. 6,601,613 B2 describes an apparatus and method for passive liquid valving in a fluidic circuit, by employing a local modification to the dimensions or surface properties of a microchannel. The modification structure is selected from the group consisting of a hydrophobic patch, a surface tension patch, hydrophobic short channel narrowing, a hydrophilic short channel narrowing and a hydrophilic channel widening. The disclosure mentions tuning of the resistance in order to enable differential passive valving, but does not describe a mechanism to do so. Moreover, the disclosure describes a tree network in which daughter channels branch from a downstream end of a parent channel. The valving principles employed appear not to offer a high level of stability, as careful attention is paid to balancing the hydrodynamic resistance.

U.S. Pat. No. 6,637,463 describes a multichannel microfluidic system intended to distribute liquid over multiple channels after injection into a single inlet channel employing passive valves, similarly to the principle described in U.S. Pat. No. 6,601,613 B2. This document also discloses balancing of the hydrodynamic resistances for the various flowpaths, and omits a mechanism to tune the stability of the passive valving structures.

US2007/0280856 A1 describes another tree network of fluidic chambers. The chambers contain "physical modifications" to prevent bubble formation. The chambers to be filled are fillable also without the physical modification. Moreover, the patent does not disclose any differential valving mechanism.

The technology of phaseguides gives rise to terminology that is used to convey context-specific meanings. The following brief glossary assists to explain certain terms used herein, although these definitions are intended to be non-limiting:

Aliquoting: refers to aliquot delivery; the insertion or portioning of a precise amount of liquid into a volume.

Common conduit: a conduit for liquid or one or more liquid-based mixtures, suspensions, to emulsions or compounds having two or more inlets branched therefrom for supply of such liquids to and emptying of such liquids from a plurality of volumes or venting of a volume.

Conduit: a channel, tube or pipe via which liquid or one or more liquid-based mixtures, suspensions, emulsions or compounds (herein "liquid-based substances") may be conveyed in the apparatus of the invention.

Confined aliquoting: refers to aliquoting of a precise amount of liquid into a volume that is larger than the liquid volume to be aliquoted.

Confining phaseguide: a phaseguide inside a volume that is intended to confine a liquid or a liquid-based mixture, suspension, emulsion or compound to a sub-volume that is less than the whole.

Contour phaseguide: a phaseguide that confines a liquid volume in close approximation to a final envisioned shape. A contour phaseguide determines the contour of a second liquid, before being brought into contact with e.g. a first liquid that is already present in the chamber or before filling of a chamber.

Counter substrate: substrate facing the substrate on which phaseguides are patterned.

Dead angle phaseguide: type of supporting phaseguide that assures filling extremes of a volume, typically corners.

Feeding conduit: a conduit typically but not necessarily branched from a supply conduit for the purpose of supply of liquid to or withdrawal of a liquid from a volume.

Inlet: a conduit for liquid or one or more liquid-based mixtures, suspensions, emulsions or compounds via which a volume containing at least one phaseguide may be filled with such liquid or emptied thereof.

Liquid-based substance: a liquid or a liquid-based mixture, suspension, emulsion or compound.

Liquid merging: the process of two miscible liquid-based substances contacting one another and starting to behave as one liquid.

Meniscus pinning: a situation in which a phaseguide prevents advancement or recession of a meniscus beyond a point at which the phaseguide retains the meniscus.

Metering: the separation of a precise, "aliquoted" amount of liquid from the bulk liquid Phaseguide: in addition to the definitions given elsewhere herein, one may regard a phaseguide as a line of material or a geometrical shape that spans the complete length, width or height of a meniscus and represents a pressure barrier for advancement or recession of this meniscus.

Phaseguide overflow; overflow: the process of a liquid or liquid-based substance intentionally, controlledly flowing over (breaching) a phaseguide at a location at which the liquid/liquid-based substance possesses sufficient energy to breach the phaseguide.

Phaseguide substrate: substrate on which phaseguides are patterned or otherwise exist.

Processing: mixing, sampling, assaying, testing, observing or assessing.

Stability: an indication of the fluid pressure required for a phaseguide or part thereof to be breached by the flow of a liquid-based substance.

Supply conduit: a conduit having one or more common feeding conduits branched therefrom.

Supporting phaseguide: a phaseguide inside a volume that determines the advancement or recession direction of a meniscus during filling or emptying of the volume.

Venting: causing or permitting the removal of a substance in liquid or gaseous form from a volume or region via a venting conduit.

Venting conduit: a conduit via which venting may occur.

Walls: substrates intersecting one or more phaseguides and/or counter-substrates.

2D Phaseguide: a phaseguide that lies in a common plane with the top-, bottom- or other surface of a volume containing the phaseguide.

3D phaseguide: a phaseguide that protrudes into a volume from a surface thereof or a cavity or channel inside a bulk material.

The concepts of phaseguide overflow and phaseguide stability are illustrated and is explained in the following section:

Phaseguide Overflow and Phaseguide Stability

A liquid-air interface typically consists of three interfaces: liquid-solid, liquid-air and air-solid. Such an interface can be sub-divided into two scenarios:

1) a hydrophilic system, in which the liquid-air interface has a contact angle with the solid phase of less than 90°;
2) a hydrophobic system, in which the liquid-air interface has a contact angle with the solid phase of more than 90°.

A similar division can be made for a liquid-liquid interface:

3) a system, in which the first liquid has a contact angle with the solid phase of less than 90°;

4) a system, in which the first liquid has a contact angle with the solid phase of more than 90°.

Phaseguides can be of use in all four situations. The barrier effect in Cases 1) and 3) is the same, and is different from Cases 2) and 4). This is illustrated by FIG. 1.

In a hydrophilic system, in FIG. 1 numeral 1 represents liquid and numeral 2 air. This arrangement is inverted in a hydrophobic system.

FIG. 1c and FIG. 1f show meniscus pinning in both directions. It is clear that the pinning effect is different, depending on whether the system is hydrophobic or hydrophilic, and whether the liquid is advancing or receding. Therefore we define meniscus pinning and phaseguide overflow in two directions:

1) Forward flow/forward pinning/forward overflow occurs when the (hydro)philic phase is advancing;
2) Reverse flow/reverse pinning/reverse overflow occurs when the (hydro)philic phase is receding.

Forward pinning and reverse pinning therefore result in different liquid behaviour and represent a pressure barrier of different stability depending on the direction of fluid advancement or recession.

The information described above in relation to FIG. 1 results in definitions of forward and reverse directions that are specific to the example illustrated in FIG. 1. A more general understanding of certain terms used in relation to phaseguide stability may be gained from the following:

Upstream, Downstream, Filling and Emptying

As generally used herein the terms "upstream" and "downstream" are defined in relation to the direction of advancement of a fluid-fluid meniscus. One may judge the relatively upstream and downstream parts differently depending on whether the meniscus is viewed from one side (i.e. as though the observer is in one fluid defining the meniscus) or the other (as though the observer is in the other fluid).

One way therefore of regarding the terms is to say that the upstream part of a fluidically interconnected network is that from which the meniscus is advancing; and the downstream part is that in which the meniscus is advancing.

The action of filling a fluidic network using this definition refers to an advancing fluid-fluid meniscus in which the upstream fluid is a liquid based substance and the downstream fluid is a gas, typically but not necessarily air.

The action of emptying a fluidic network refers to an advancing fluid-fluid meniscus in which the upstream fluid contains a gas, typically air, and the downstream fluid is a liquid based substance.

Phaseguide stability is typically defined in two directions and depends on the direction of advancement of the fluid-fluid meniscus. Moreover the question of what is regarded as the upstream and what is the downstream part of a network typically will vary depending on the direction in which the meniscus is moving. In view of this it often requires a context- and application-specific approach to determining the relatively upstream and downstream parts of the network forming part of the apparatus of the invention.

An important parameter for a 3D phaseguide is the draft angle of the side wall of the phaseguide. The draft angle of the side wall is defined as the deviation from the normal of the counter substrate. A typical draft angle is 0°, meaning that the sidewall of the phaseguide is normal to the counter substrate. However, for manufacturing purposes, draft angles up to 10° may be required (as is for instance of importance for the release of plastic moulded parts from their moulds).

A maximum draft angle depends on the complete set of wettability properties of the phaseguide and counter substrate. It should preferably be smaller than 45° more preferably smaller than 10° and most preferably close to 0°. Negative draft angles would yield even more stable phaseguides, however such arrangements may meet with practical limitations of fabrication.

This is also of importance for defining phaseguide stability. WO2010/086179 A2 describes how phaseguide stability could be tuned by designing a v-shaped feature of the phaseguide in at least four ways:

As a small phaseguide wall interface angle (see FIGS. 2a to 2c hereof);

As a V-shape bend along the phaseguide (see FIGS. 2d to 2f);

As a branch along the structure (see FIGS. 2g to 2i);

As an inlet formed in the phaseguide.

A particularly high degree of stability control by angles and their radii is obtained when the meniscus becomes stretched between the phaseguide edge and the counter substrate. This is typically the case when the counter substrate is more hydrophilic than the phaseguide material. We typically observe an excellent control of phaseguide stability when working with glass counter substrates having an advancing contact angle of around 20° and a phaseguide material contact angle of around 70°. Therefore, a strongly hydrophilic top substrate with a contact angle of less than 45°, more preferably less than 30°; and a less hydrophilic phaseguide material with a contact angle larger than 45° more preferably larger than 60°, are beneficial to give control over the phaseguide stability by angle variations.

In order to create a stable phaseguide barrier, the smallest angle along a phaseguide (including phaseguide wall, branch or bend) needs to be larger than a critical angle as defined by the Concus-Finn theorem:

$$a_{crit} = 180° - \theta_1 - \theta_2$$

Here $\theta_1$ and $\theta_2$ are respective contact angles on both sides of the angle (i.e. the wall material and the phaseguide material). For a sharp V-bend and for most branch configurations $\theta_1$ and $\theta_2$ have the same value. This is also the case for phaseguide-wall angles when both are made out of the same material.

Additionally to angle variation, phaseguide stability can be tuned by variation of the radius of an angle. A large radius results in a higher stability then a small radius. Clearly a combination of angle and radius tuning can also be explored. As the pressure drop over a meniscus varies with the sum of the inverse of the two principal radii of the meniscus, the tuning of the phaseguide stability is most effective for small radii. In practice stability tuning by using variations in angles is preferred over variation in radii.

Other methods to tune the stability of the phaseguide can be thought of, including adjusting the draft angle of the 3D phaseguides, the draft angle of the side wall, the height of 3D phaseguides; and the wettability and the geometry of the channel network for both 3D and 2D phaseguides. Again, in practice the most versatile manner to tune a phaseguide stability is by angle variation of bends, branches, phaseguide wall interfaces or inlets as mentioned above.

In all drawings in FIG. 2 overflow will occur at the smallest angle, in this case a2. The same principle counts for reverse flow (see FIGS. 3a to 3i).

The angles for which overflow can be predicted are not necessarily the same for forward and reverse flow.

From FIGS. 2 and 3 it becomes clear that selective phaseguide overflow can be established, once a bulk liquid faces multiple phaseguides at the same time. This is illustrated in FIGS. 4a and 4b.

FIG. 4a shows a liquid volume pinned on two phaseguides simultaneously. Under application of a forward pressure on the liquid (signified by arrows in FIG. 4b), overflow occurs at the least stable phaseguide. In this case this is the phaseguide on the right, that has a sharp V-shaped bend.

FIG. 5a shows again a liquid pinned on two phaseguides. Under application of a reverse pressure (see the arrows in FIG. 5b), overflow will occur at the least stable phaseguide. This is again the phaseguide on the right, that has a sharp V-shaped bend.

Stability of the phaseguide depends on the flow direction. If this direction is reversed, such as in FIG. 5, the stability changes as indicated above.

FIG. 6 shows a zigzag-shaped phaseguide that exhibits reduced stability under both forward and reverse pressure.

SUMMARY OF THE INVENTION

Broadly, the invention relates to structures that make use of basic phaseguide structures as disclosed in WO2010/086179 A2. The invention also relates to methods of using such structures.

In particular in the field of microfluidics there are needs for the controlled processing of liquids and combinations of liquids. Examples of occasions when fluidics techniques involving phaseguides are helpful include but are not limited to assaying; combinatorial chemistry, analytical chemistry, synthetic chemistry, clinical testing, sample preparation, separation techniques, in-vitro fertilization, gene knock-out and knock-down, cell transfection, tissue culturing, crystallization experiments, combinatorial pharmacology and biotechnology; cell culturing; spectrophotometry; and all manner of related testing and experimental activities.

According to the invention in a first aspect there is provided apparatus for processing liquids or liquid-based substances, the apparatus comprising a plurality of volumes at least two of which are defined at least in part by one or more phaseguides inside the volume and/or in a conduit connected thereto for controlling aliquoting of one or more liquids or liquid-based substances inside the volume, each volume having an upstream and downstream side with respect to a meniscus movement direction defined during filling of the volume with or emptying of the volume of one or more liquids or liquid-based substances, the apparatus including at least one common upstream-side conduit connected to supply a fluid, especially a liquid or liquid-based substance via a plurality of the inlet or extraction conduits, a plurality of the phaseguides exhibiting a predetermined level of stability and one or more of the phaseguides exhibiting a predetermined different stability compared with the stability of at least one of the other phaseguides whereby to control the preference order in which overflow of the phaseguides occurs during filling and/or emptying of at least one said volume; the said stability being determined by the value and radius of an acute angle along a said phaseguide at the downstream side of the phaseguide.

More broadly in accordance with the invention there is provided an apparatus for processing liquids or liquid-based substances, the apparatus comprising a plurality of volumes each defined at least in part by one or more phaseguides for aliquoting a precise amount of one or more liquid-based substances in the volume, each volume including two or more respective inlets via which it may be filled with one or more liquid-based substances and being connected to at least one vent for venting substances expelled during filling and/or emptying, the apparatus including a common feeding conduit connected to the said plurality of volumes.

According to a second aspect of the invention there is provided apparatus for processing of liquids or liquid-based substances comprising a plurality of volumes at least two of which are defined at least in part by one or more phaseguides inside the volume and/or in a conduit connected thereto for controlling aliquoting of one or more liquids or liquid-based substances inside the volume, each volume having an upstream and downstream side with respect to a meniscus movement direction defined during filling of the volume with or emptying of the volume of one or more liquids or liquid-based substances, the apparatus including at least one common upstream-side conduit connected to supply a fluid, especially a liquid or liquid-based substance, via a plurality of the inlet or extraction conduits, a plurality of the phaseguides exhibiting a predetermined level of stability and one or more of the phaseguides exhibiting a predetermined different stability compared with the stability of at least one of the other phaseguides whereby to control the preference order in which overflow of the phaseguides occurs during filling and/or emptying of at least one said volume; the apparatus being operative to confine a first liquid or liquid-based substance in a said volume before permitting addition of a second said liquid or liquid-based substance.

In one preferred embodiment of the invention at least one said volume includes or is associated with an upstream-side phaseguide in or associated with a first said volume that is of lower stability than at least one other downstream-side phaseguide in or associated with at least one second said volume. This arrangement may optionally be referred to as providing an excess flow reservoir. Such an arrangement is useful when it is required to fill a volume forming part of a series, network or array with a chosen quantity of liquid and then readily accommodate any excess liquid over and above the chosen quantity.

In another preferred embodiment of the invention the apparatus includes at least one phaseguide that is a protrusion into the phaseguide substrate, the said protrusion being defined by a first side and a second side permitting meniscus overflow and said first and second sides each being a sidewall of the phaseguide, each sidewall having a draft angle with respect to a normal to a counter substrate that is less than 45°, the phaseguide having an intersection at each end with a channel or chamber wall, and the phaseguide sidewall further having a wettability leading to a contact angle with respect to an advancing or receding meniscus that is larger than the contact angle of a said meniscus with the counter substrate.

In yet another preferred embodiment of the invention the apparatus includes at least one phaseguide that is a protrusion into a channel, the said protrusion being defined by first side and a second side permitting meniscus overflow and said first and second sides being sidewalls of the phaseguide, each side having a draft angle with respect to a normal to a counter substrate that is less than 45°, the phaseguide having an intersection at each end with a channel or chamber wall, and the phaseguide sidewall further having a wettability leading to a contact angle with respect to an advancing or receding meniscus that is larger than the contact angle of the meniscus with the counter substrate.

The foregoing features of the design of the apparatus advantageously are based on knowledge of the Concus-Finn equation set out above.

According to a third aspect of the invention there is provided a method of filling or partially filling a plurality of volumes with a liquid or liquid-based substance, the said volumes being connected in a series, network or array by one or more conduits; the series, network or array including upstream and downstream portions when judged with reference to a direction of movement of a liquid-liquid or liquid-gas meniscus; and the series, network or array including at least a relatively upstream-positioned phaseguide and a relatively downstream-positioned phaseguide, the relatively upstream-positioned and relatively downstream-positioned phaseguides exhibiting differing stabilities from one another, the said stabilities depending on the value of an acute angle subtended by a formation with the downstream side of each said phaseguide, and also on the dimensions of a radius defined at the intersection of the formation and the associated said phaseguide, the method comprising arranging or selecting the stabilities of the relatively upstream-positioned and relatively downstream-positioned phaseguides to determine the order of filling of the plurality of volumes; and performing a filling step such that overflow of the phaseguides takes place in a predetermined order determined by the phaseguide stabilities.

According to a fourth aspect of the invention there is provided a method of filling one or more volumes with or emptying one or more volumes of a liquid or liquid-based substance, the said volumes being connected in a series, network or array by one or more conduits; the series, network or array including at least a downstream portion when judged with reference to a direction of movement of a liquid-liquid or liquid-gas meniscus, and the series, network or array including two or more phaseguides that are positioned relatively downstream of a said volume, the method including the steps of selecting the stability of a said relatively downstream-positioned phaseguide that lies relatively far, in the series, network or array, from the relatively upstream origin of a said conduit to be less than the stability of a said relatively downstream-positioned phaseguide that lies relatively near, in the series, network or array, to the origin of the said conduit; and performing a filling or emptying step such that overflow of the phaseguides takes place in a predetermined order determined by the phaseguide stabilities.

According to a fifth aspect of the invention there is provided a method of isolating one or more liquids or liquid-based substances in one or more volumes forming part of a series, network or array including one or more connected conduits, the series, network or array including upstream and downstream portions when judged with reference to a direction of movement of a liquid-liquid or liquid-gas meniscus; and a relatively downstream conduit of the series, network or array having branchingly connected thereto a said volume and including therein a phaseguide positioned relatively downstream from an origin of the conduit together with a further phaseguide positioned relatively upstream with reference to the origin of the conduit, the relatively downstream-positioned phaseguide being of lower stability than the further phaseguide; and the method including the steps of causing partial emptying of the volume whereby liquid or a liquid-based substance flows over the relatively downstream-positioned phaseguide so as partially to empty the conduit while causing retention of liquid or a liquid-based substance in the volume.

According to a sixth aspect of the invention there is provided a method of causing contact, in a volume connected in a series, network or array by one or more conduits and the series, network or array including upstream and downstream portions when judged with reference to a direction of movement of a liquid-liquid or liquid-gas meniscus, the said volume including two or more phaseguides defining first, second and third parts of the volume and each said part being connected to a respective said conduit of the series, network or array, a relatively downstream-positioned said conduit being connected to the second part of the volume that is defined between the two said phaseguides in the volume and respective relatively upstream-positioned said conduits being connected to the first and third parts of the volume, the method including the steps of causing or permitting filling of liquid or a liquid-based substance into the first and third parts of the volume; causing or permitting breaching of a said phaseguide by a liquid or liquid-based substance; and causing or permitting filling of a further liquid or liquid-based substance into the second part of the volume such that contact between the liquids or liquid-based substances occurs.

According to a seventh aspect of the invention there is provided a method of causing partial removal, from a volume connected in a series, network or array by one or more conduits and the series, network or array including upstream and downstream portions when judged with reference to a direction of movement of a liquid-liquid or liquid-gas meniscus, the said volume including two or more phaseguides defining first, second and third parts of the volume and each said part being connected to a respective said conduit of the series, network or array, the second part of the volume being defined between the two said phaseguides in the volume, the method including the steps of causing or permitting emptying of liquid or a liquid-based substance from the second part of the volume; causing or permitting breaching of a said phaseguide by a liquid or liquid-based substance; and thereby causing or permitting emptying of the first and/or third part of the volume such that the volume becomes partially vacated.

Disclosed herein is a method of operating an apparatus for processing liquids or liquid-based substances, the apparatus comprising a plurality of volumes each containing one or more phaseguides for aliquoting a precise amount of one or more liquid-based substances inside the volume, each volume including two or more respective inlets via which it may be filled with one or more liquid-based substances and being connected to at least one vent for venting substances expelled during filling and/or emptying, the method comprising the step of causing a liquid-based substance to fill, via one or more of the inlets, one or more of the volumes until the liquid-based substance becomes pinned at a chosen phaseguide in each of the said volumes thereby causing a predetermined quantity of the liquid-based substance to reside in each volume, the liquid-based substance during filling expelling any pre-existing fluid substances of different wettability than the liquid-based substance in each said volume via the vent thereof, the apparatus including a common feeding conduit connected to the said plurality of volumes.

Optional features of the invention are defined in the dependent claims.

For the avoidance of doubt it is hereby stated that the various distinct aspects and features of the invention may in addition be provided in any viable combination.

Thus for example the two apparatus aspects may be present in one and the same embodiment of the invention; and for instance two or more of the method aspects may be carried out in conjunction with one another.

Such combinations of method steps may depending on the precise circumstances be carried out sequentially or in some cases simultaneously.

The invention resides in all such combinations of integers and/or method steps as would occur to the worker of skill based on the disclosure herein.

There now follows a description of preferred embodiments of the invention, by way of non-limiting example, with reference being made to the accompanying drawings in which:

FIGS. 1a to 1g illustrate various types of meniscus pinning that are possible using phaseguides. The pinning types that arise depend on whether the system is hydrophilic or hydrophobic, and on the design of the phaseguide;

FIGS. 3a to 3i illustrate ways of "tuning" reverse flow phaseguide stability;

Figures 2A, 2B, 2C:
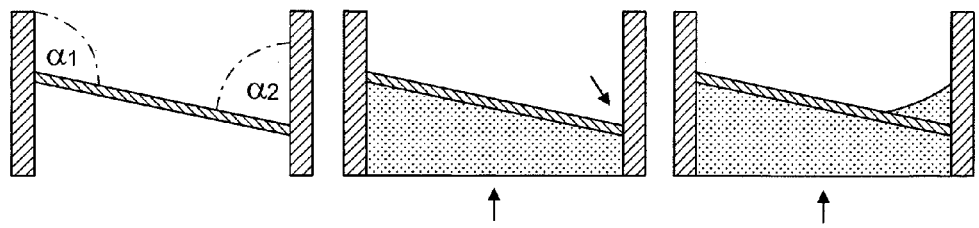
FIGS. 2a to 2i illustrate ways of "tuning" forward flow phaseguide stability.
Figures 2D, 2E, 2F:
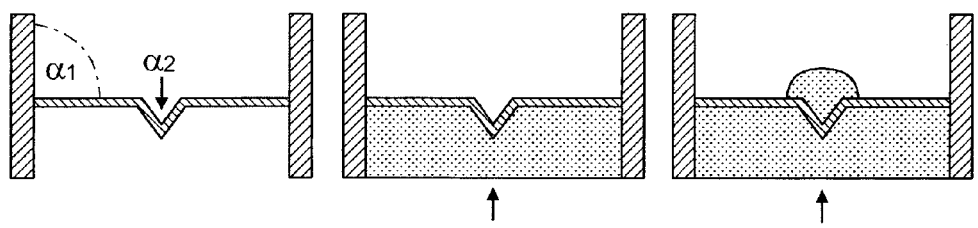
Figures 2G, 2H, 2I:
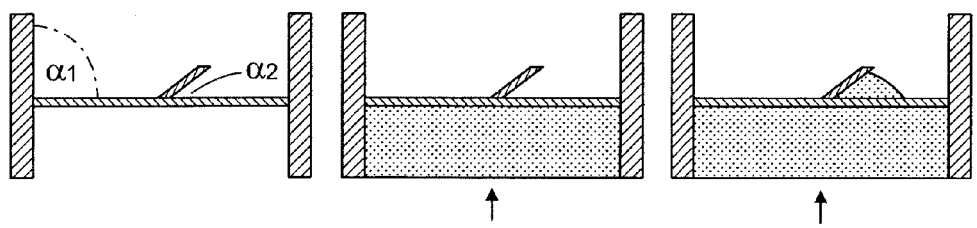
Figure 4:
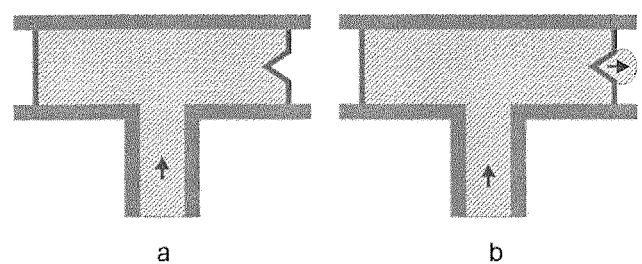
Figure 5:
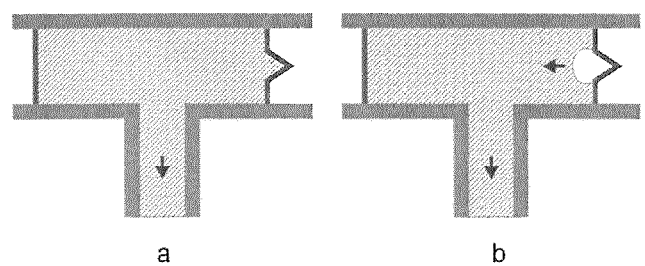
Figure 6:
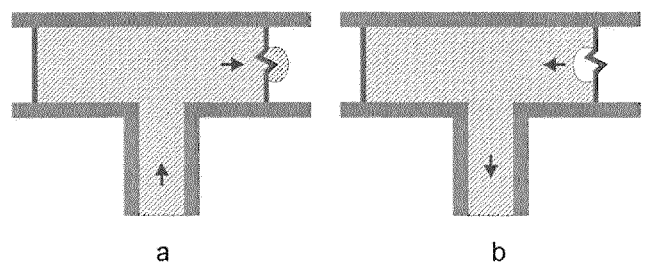
Figure 9A:
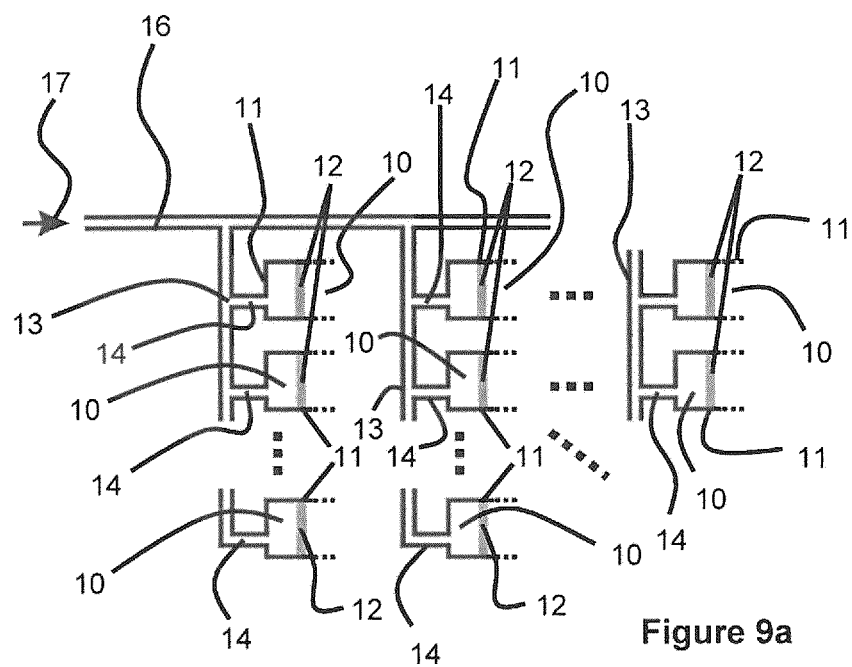
Figure 9B:
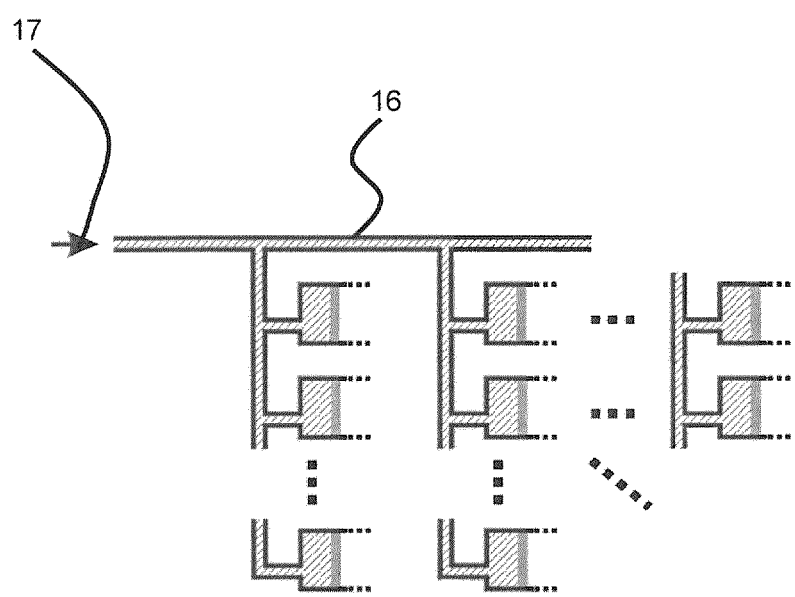
Figure 10A:
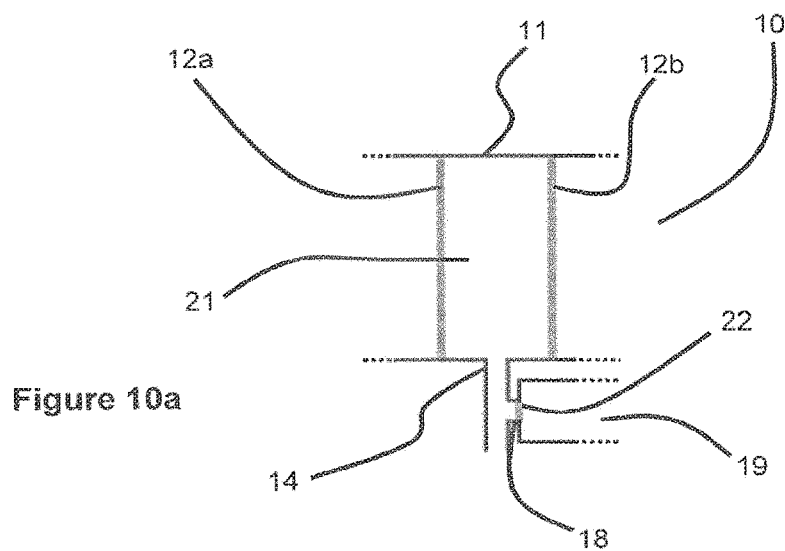
Figure 10B:
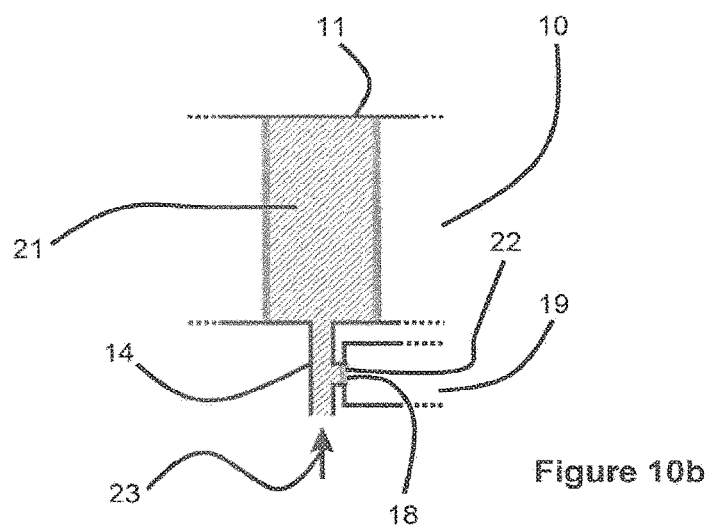
Figure 10C:
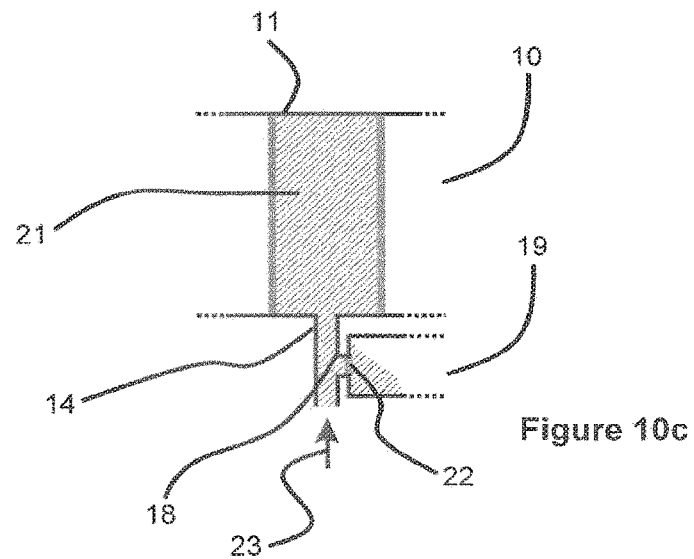
Figure 11A:
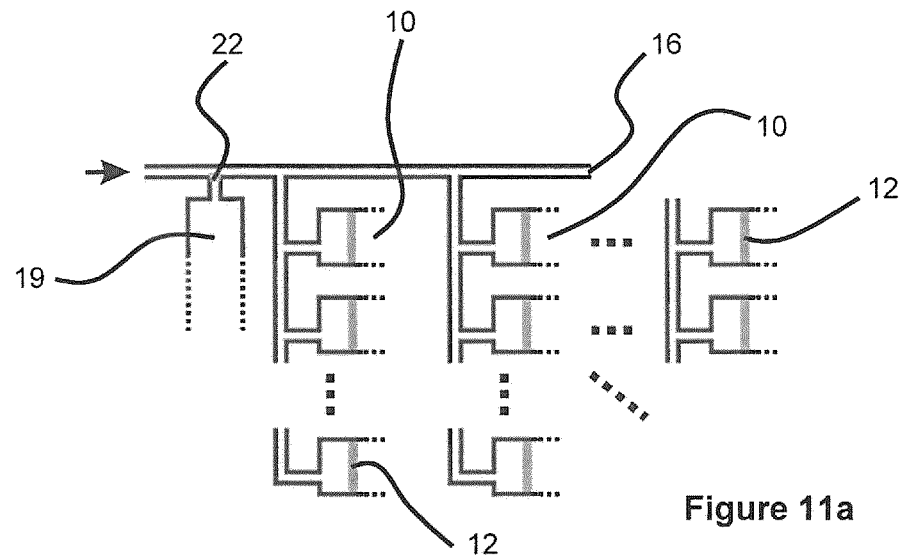
Figure 11B:
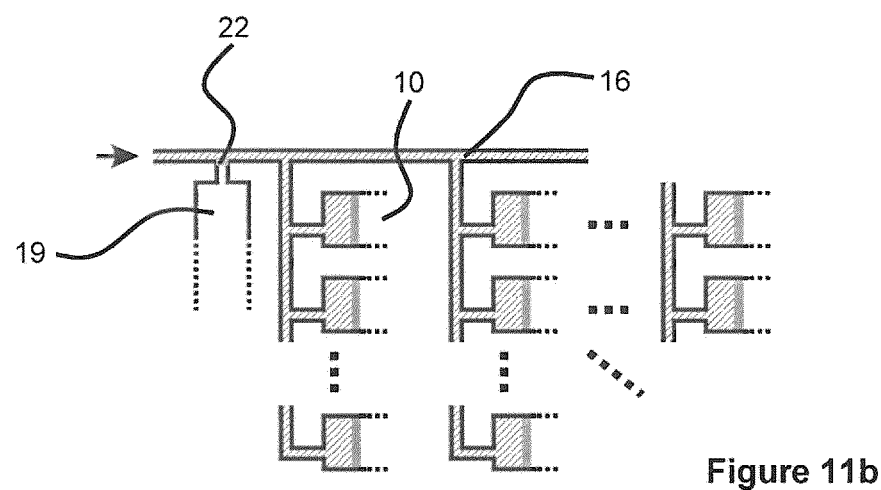
Figure 11C:
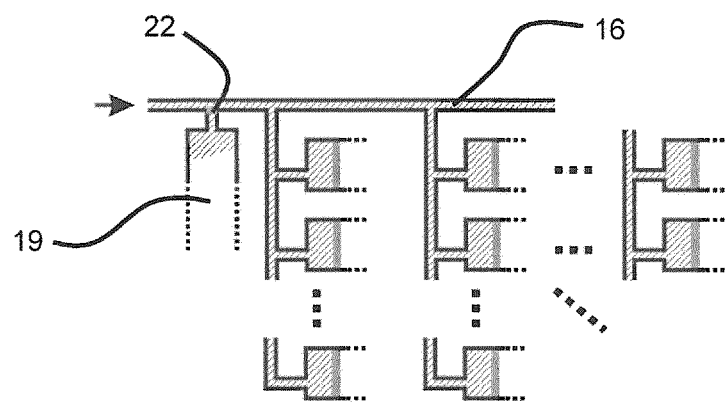
Figure 12A:
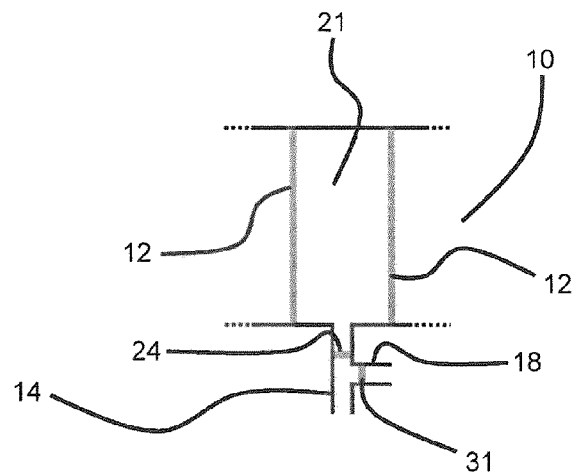
Figure 12B:
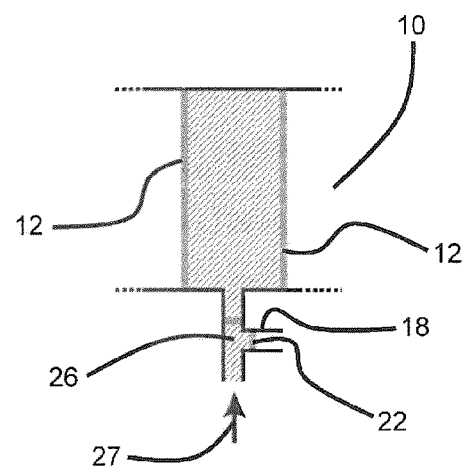
Figure 12C:
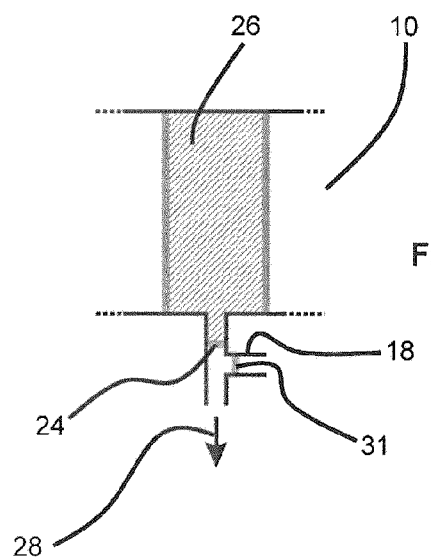
Figure 14A:
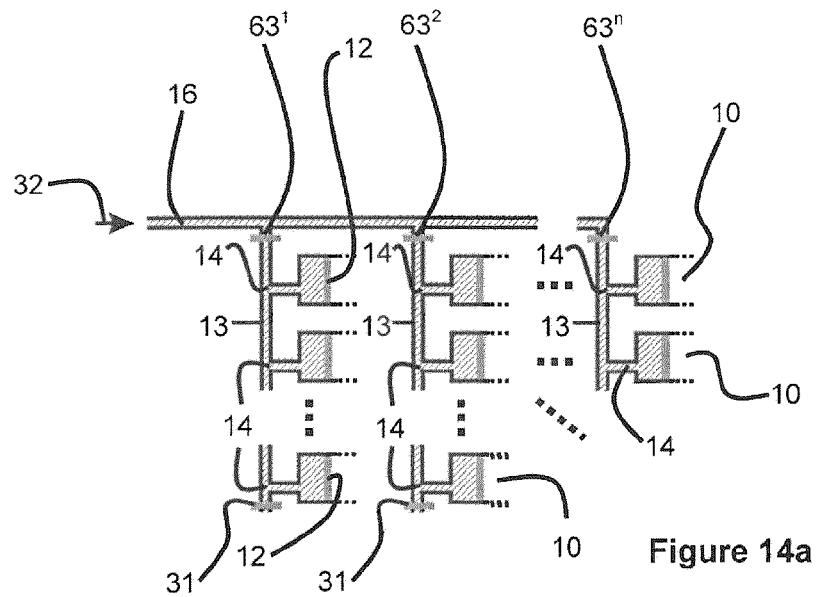
Figure 14B:
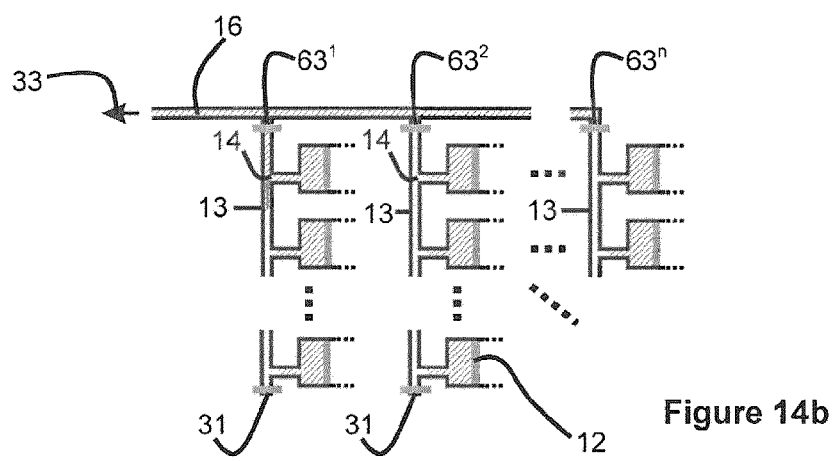
Figure 14C:
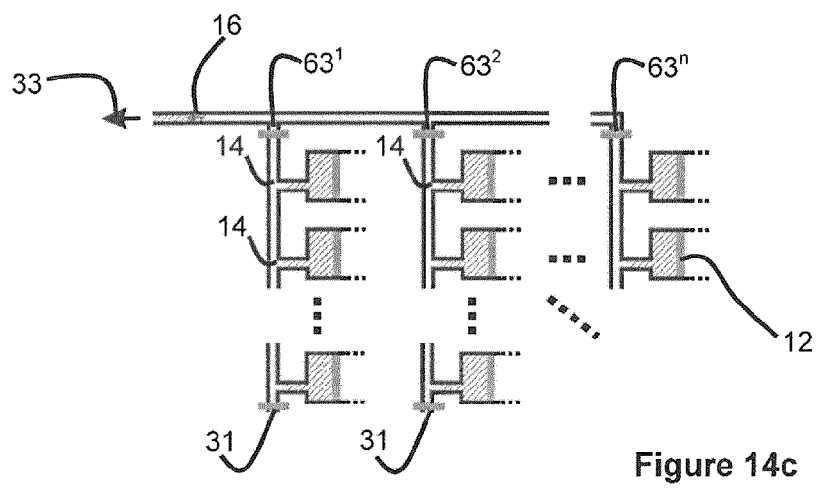
Figures 15A, 15B, 15C:
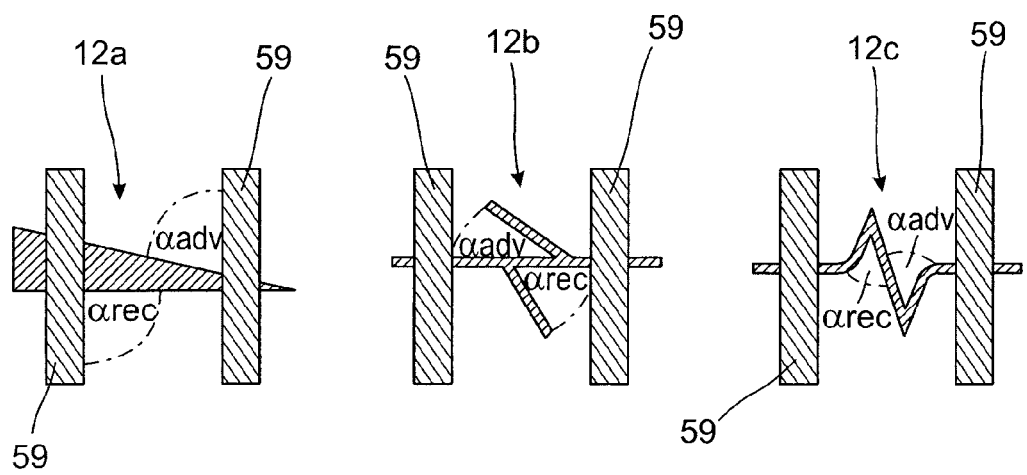
Figure 16A:
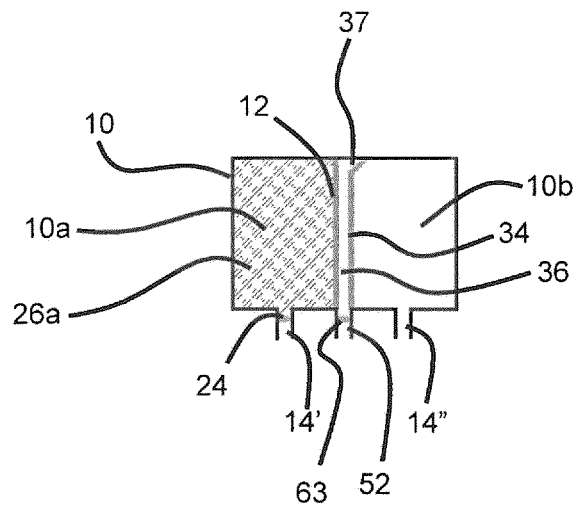
Figure 16B:
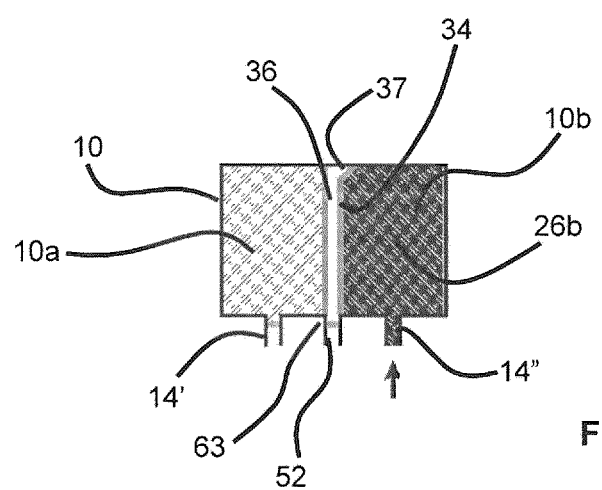
Figure 16C:
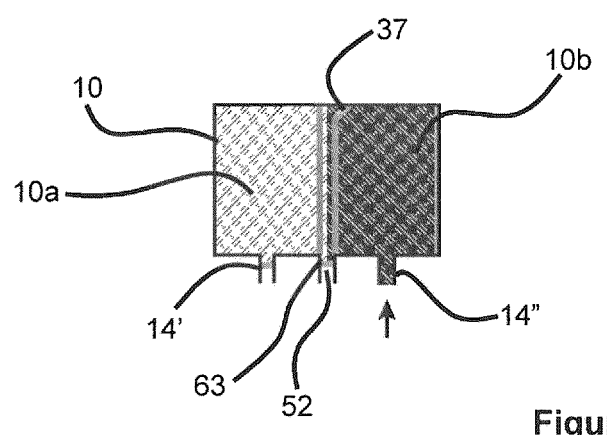
Figure 17A:
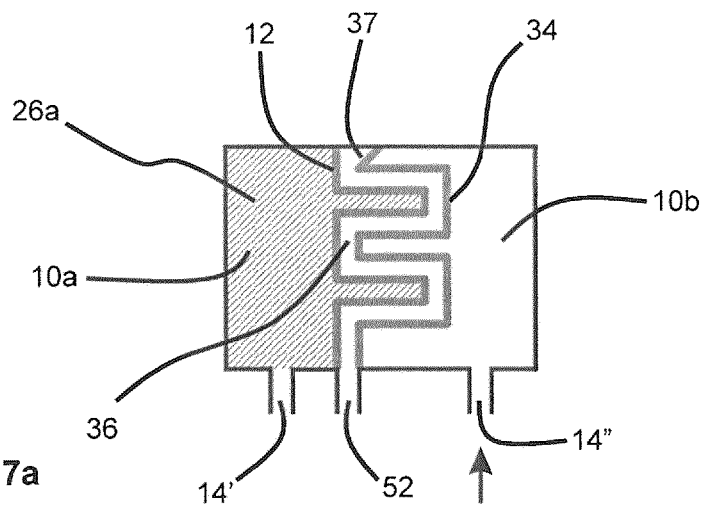
Figure 17B:
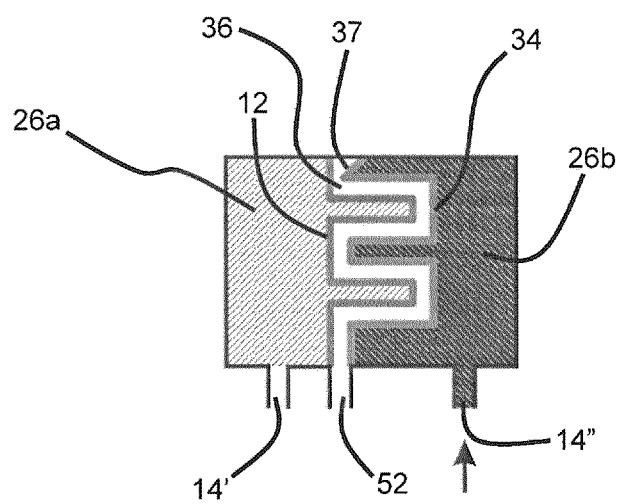
Figure 17C:
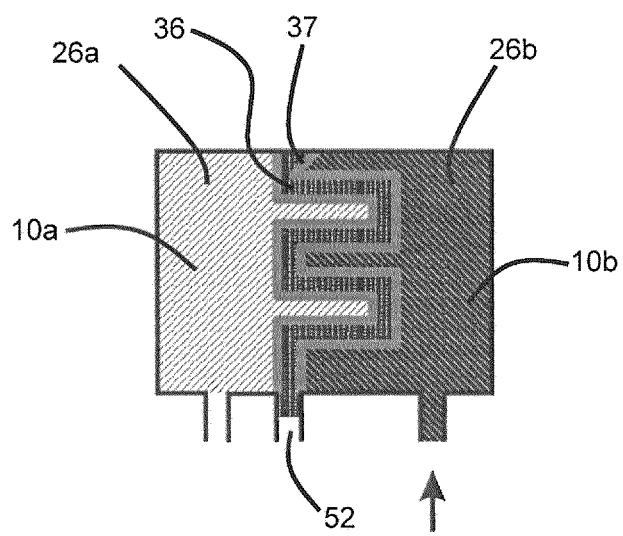
Figure 18A:
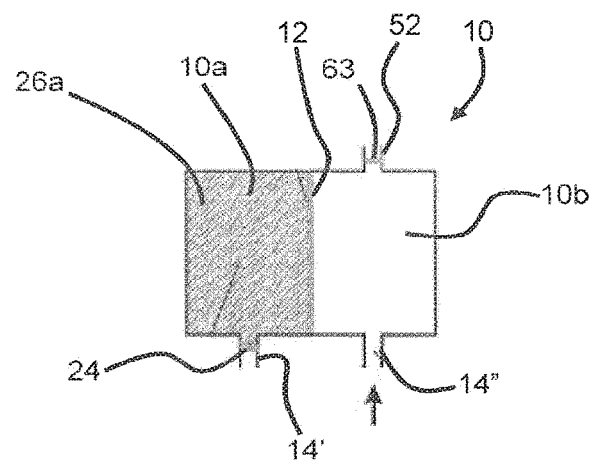
Figure 18B:
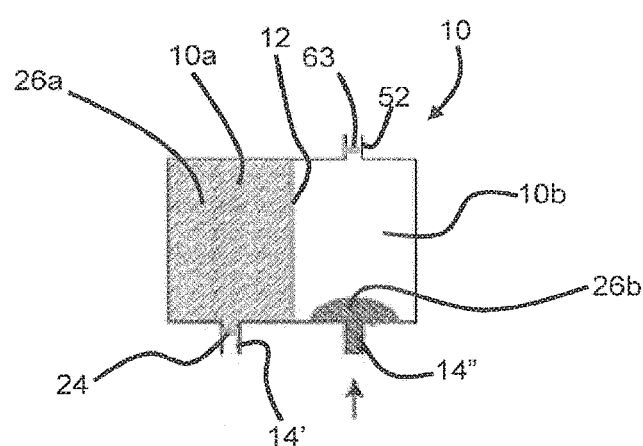
Figure 18C:
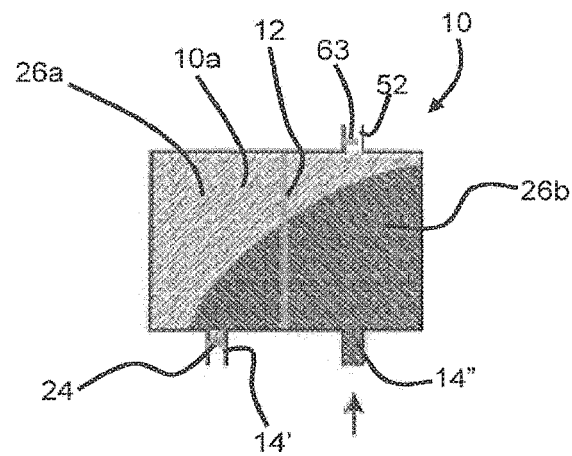
Figure 19:
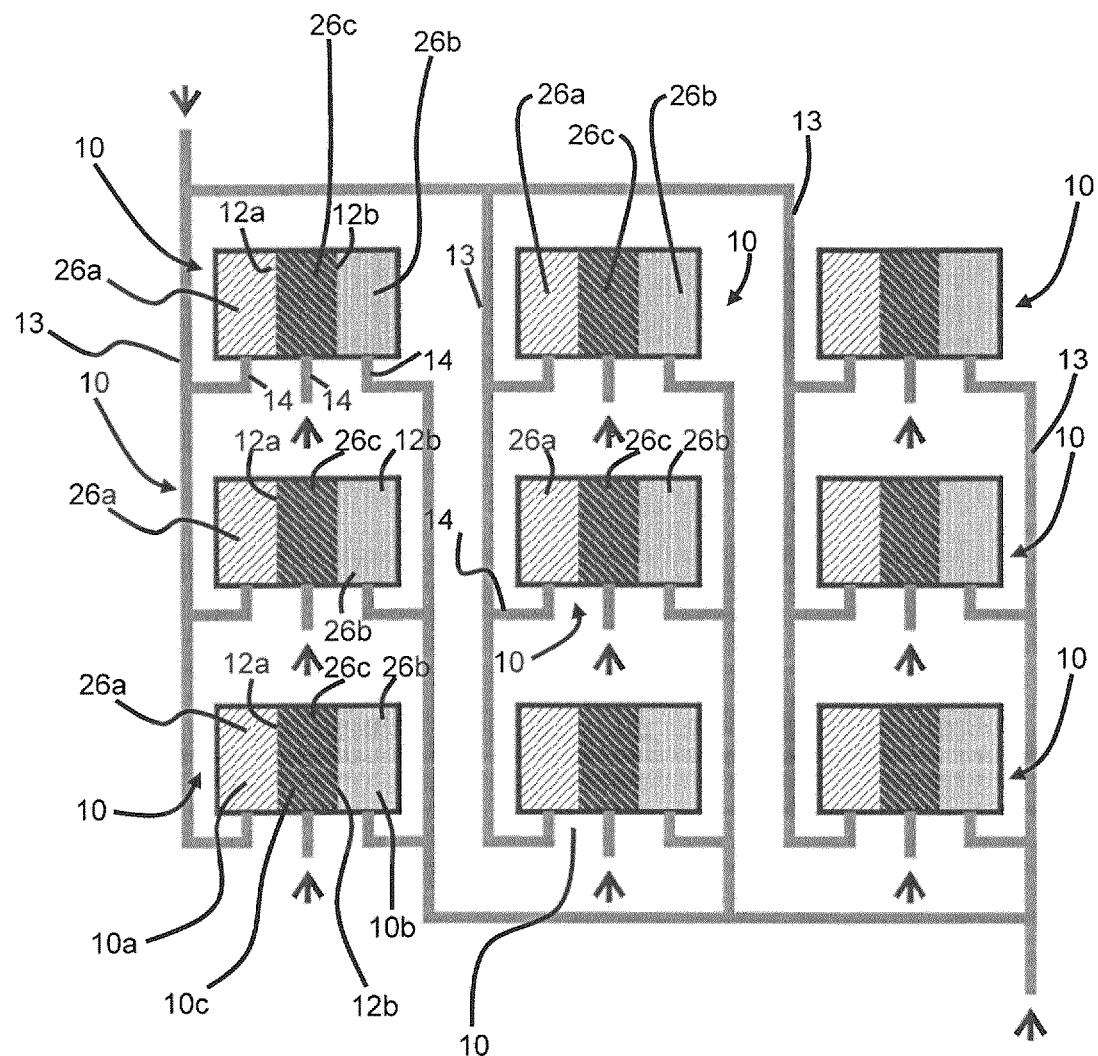
Figure 20:
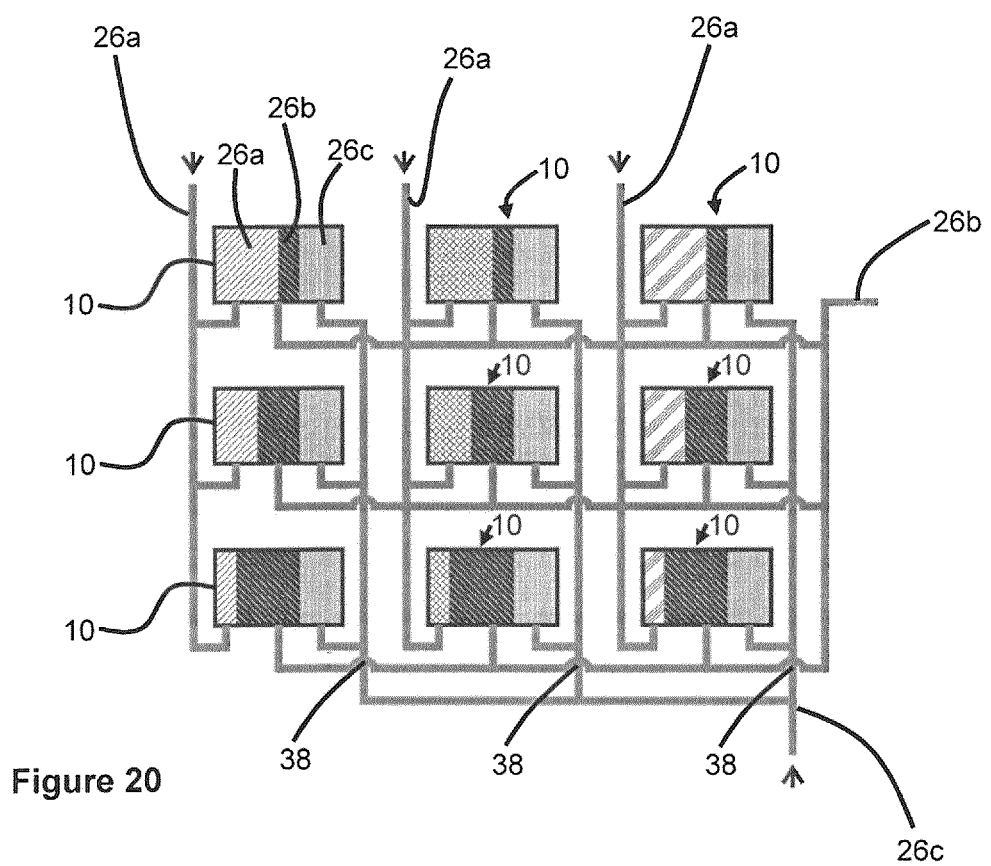
Figure 21:
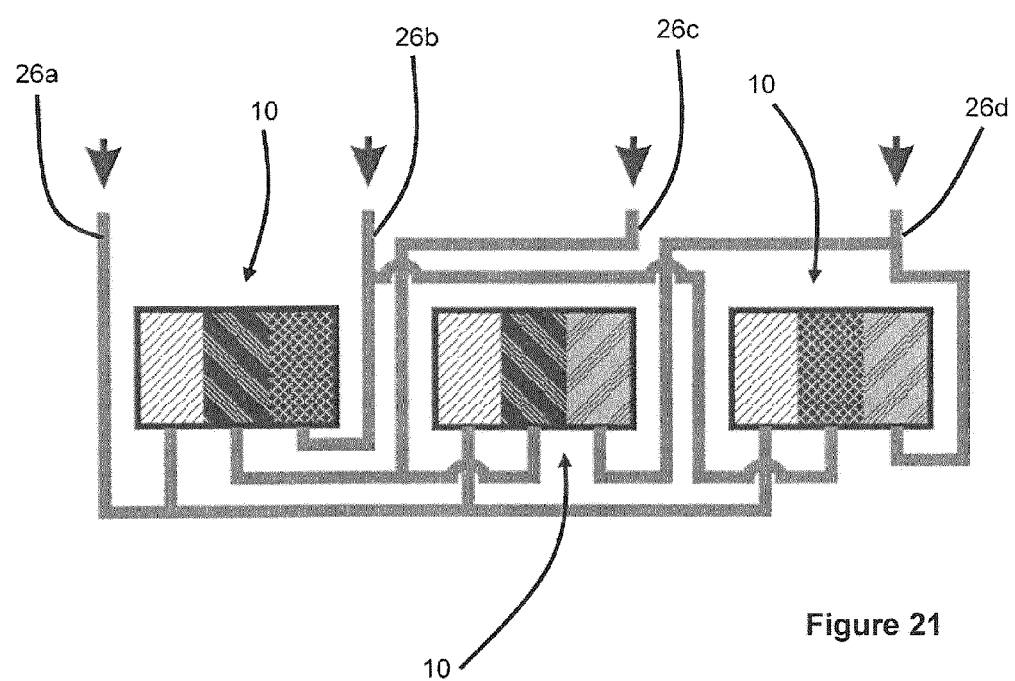

FIGS. 4a and 4b schematically show principles of selective or prioritised overflow of phaseguides;

FIGS. 5a and 5b show selective overflow when a "reverse" pressure is applied;

FIGS. 6a and 6b illustrate a phaseguide that by reason of its design is of reduced stability in both the forward and reverse flow directions;

FIGS. 7a to 7d are simplified, schematic views of a basic optional form of apparatus in accordance with the invention in which at least one liquid is aliquoted through a common feeding conduit to each of a plurality of volumes, the FIG. 7 showing the condition of the apparatus before, during and after filing;

FIGS. 8a to 8d are simplified, schematic views of a basic optional form of apparatus in accordance with the invention in which at least one liquid is emptied through a common emptying conduit from each of a plurality of volumes, the FIG. 8 showing the condition of the apparatus before, during and after emptying;

FIGS. 9a and 9b are simplified, schematic views of a basic optional form of apparatus in accordance with the invention in which at least one liquid is aliquoted through a common feeding conduit to each volume, the FIG. 9 showing the condition of the apparatus both before and after filling;

FIGS. 10a to 10c are schematic partial views showing an excess flow volume arrangement for a volume in accordance with the invention;

FIGS. 11a to 11c show in schematic form how the excess flow volume of FIGS. 10a to 10c may be incorporated into and used in conjunction with the FIG. 9 apparatus;

FIGS. 12a to 12c illustrate in schematic form a variant on the FIGS. 10a to 10c embodiment that is useful for accurate liquid metering;

FIGS. 13a to 13d schematically show an arrangement in which the principle of FIGS. 12a to 10c is applied in a multi-volume network such as that of FIG. 7;

FIGS. 14a to 14c schematically show an arrangement in which the principle of FIGS. 12a to 12c is applied in a multi-volume network such as that of FIG. 7;

FIGS. 15a to 15c show a variety of preferred phaseguide shapes that allow tuning of both forward and reverse stability in small channels;

FIGS. 16a to 16c show in schematic form another arrangement, in accordance with the invention, for controlledly mixing or causing contact between accurately dispensed quanta of liquid-based substances;

FIGS. 17a to 17c show a variant on the FIG. 16 embodiment in which a labyrinthine or meandering venting region, defined by phaseguides, results in a larger contact area between the liquid-based substances and therefore faster exchange of reagents due to diffusion, than e.g. the FIGS. 16a to 16c arrangement;

FIGS. 18a to 18c show an embodiment of the invention in which phaseguide control permits controlled multiple-liquid aliquoting and subsequent merging;

FIG. 19 shows an example of a liquid routing scheme, in which two liquids are aliquoted in through a common supply conduit and a third liquid is aliquoted for each volume individually;

FIG. 20 shows a more complex example of a routing scheme, in which three liquids are aliquoted through a common supply unit, requiring vias for crossing of microfluidic supply channels;

FIG. 21 shows a more complex example of a routing scheme, in which three liquids are aliquoted in unique combinations of two over three volumes and a fourth liquid is inserted into each volume.

Figure 22A:
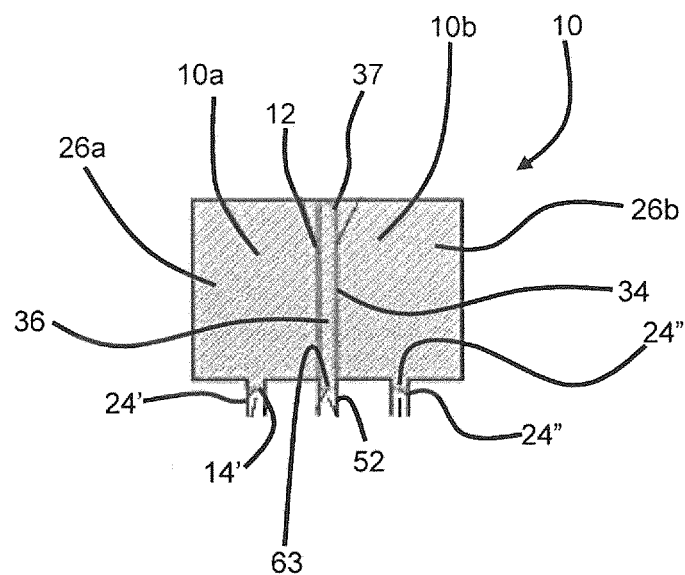
Figure 22B:
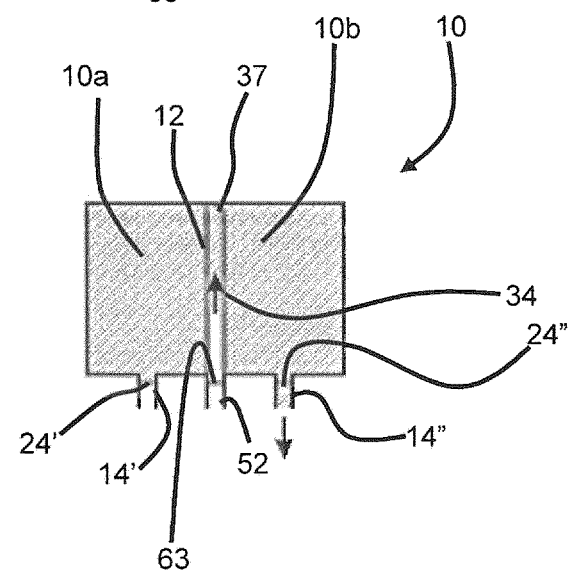
Figure 22C:
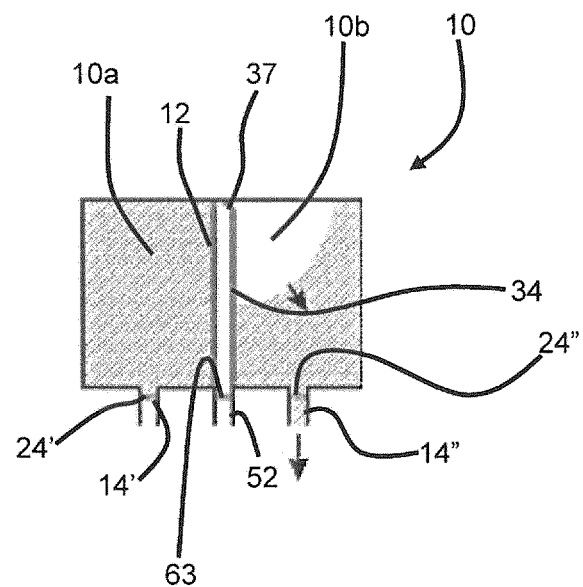
Figure 23A:
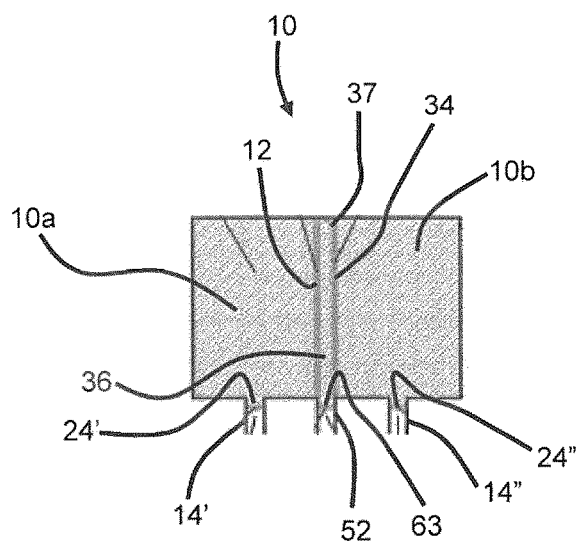
Figure 23B:
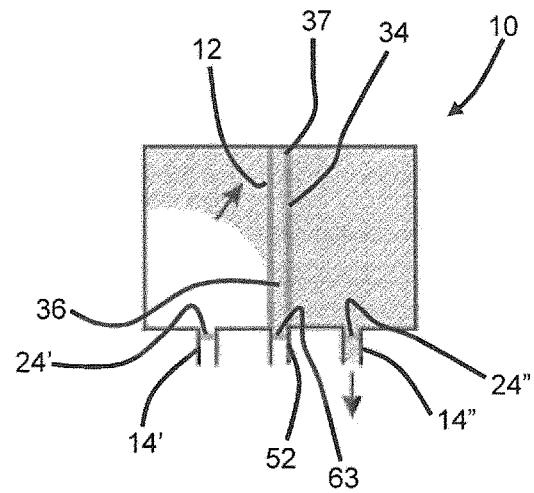
Figure 23C:
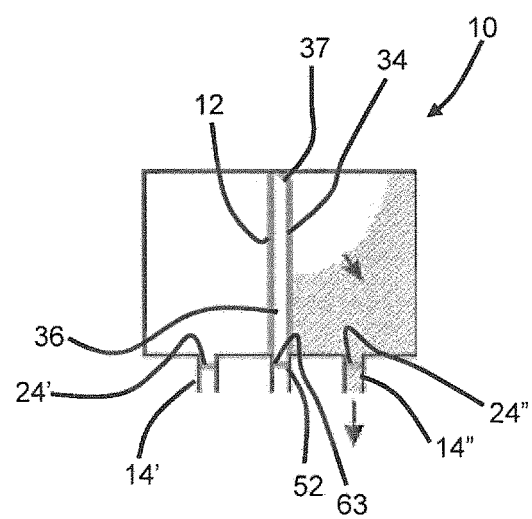

FIGS. 22a to 22c show in schematic form an embodiment of the invention that is useful in the selective recovery of a predetermined liquid portion from a volume, while causing minimal disturbance to the remaining liquid portion; and FIGS. 23a to 23c show an embodiment that is similar to FIG. 22 and is configured to permit complete withdrawal ("recovery") of liquid from a volume;

Referring to the drawings FIGS. 7a to 7b show in simplified schematic form an optional basic version of apparatus in accordance with the invention. In FIGS. 7a to 7c a plurality of volumes 10 are defined inside walled chambers or other structures 11 that may contain a volume.

In the embodiment shown each volume is rectangular when viewed in plan and all the volumes 10 resemble one another as to dimension and shape. This need not necessarily be so, however, and variations in the volume designs are possible within the scope of the invention.

The volumes preferably are of a general kind and are suitable for the mixing, assaying, testing, reacting, distributing and other processing of liquid-based substances preferably at a "microfluidics" or "nanofluidics" scale, at which phaseguides are particularly effective.

The chambers 11 may be made from a range of materials, including mixtures of materials. It is preferable that at least part of each chamber 11 is transparent or translucent such that any visible change in the contents of the chambers may be observed either by eye or using optical assessment/testing equipment.

Each volume 10 has an inlet 14 and an outlet 52, whereby the inlet 14 is connected to a common feeding conduit 13 and the outlet is connected to a common venting conduit 53. The network contains phaseguides $63^1$ to $63^n$ that are positioned either downstream from the volume with respect to the filing direction or inside the volume itself.

At least one phaseguide $63^1$ has a modified stability such that it is less stable with respect to other phaseguides depicted. The phaseguide assures a prioritized overflow, starting with the phaseguide along the common venting conduit 53 that is most distal from a venting arrangement that is not shown in FIG. 7 but that would in practice be connected at the free end 53a of venting conduit 53.

The large arrow in FIGS. 7b to 7d indicates the application of a liquid flow at an inlet end 13a of feeding conduit 13. This flow may be generated by a pressure applied to the inlet 13a or by suction applied to the venting arrangement at end 53a of conduit 53.

In FIG. 7d, the common venting arrangement 53 is partially filled with liquid. This is not always the case. In fact, in some cases it is preferable that the common venting conduit 53 is not filled with liquid during operation.

Although the common venting conduit in the embodiment illustrated corresponds with and commonly addresses a plurality of volumes, this need not be necessarily so.

Also, the common venting conduit 53 may be absent and volumes may have their own individual venting conduits.

The volumes 10 are shown larger than the channel network, but this does not necessarily need to be the case.

Also one volume may in reality be made up of multiple volumes "cascaded" one after the other.

The apparatus in FIGS. 7a to 7d may be part of a higher order network that has branches or multiple "hierarchies". In that case each branch of higher hierarchy has the same phaseguide configuration as in FIGS. 7a to 7d and in which the volumes are replaced by a branch of lower hierarchy. The stability of the less stable phaseguide of each branch should be higher than the stability of the less stable phaseguide of a sub-branch.

The apparatus of FIGS. 7a to 7d can also be used for complete recovery of fluid, as is illustrated in FIGS. 8a to 8d. The small arrow in FIG. 8c points to a phaseguide $63^1$ of lower stability with respect to the other phaseguides, by means of which the liquid is confined at a certain point during the emptying procedure. Thus, emptying of the common venting conduit 53 commences at the phaseguide related to the volume that is situated along the common venting conduit furthest from the vent.

Again actuation may be based either on suction or on the application of positive pressure (or a combination of these effects).

The apparatus in FIGS. 8a to 8d may be part of a network of multiple branch hierarchies. In that case each branch of higher hierarchy has the same phaseguide configuration as in FIGS. 8a to 8d and in which the volumes are replaced by a branch of lower hierarchy. The stability of the less stable phaseguide of each branch should be higher than the stability of the less stable phaseguide of a sub-branch.

In FIGS. 7 and 8 the liquid-filled, relatively upstream parts of the network are signified by shading.

In FIGS. 13a to 13d described below the sense of what is "upstream" and what is "downstream" is reversed relative to the FIGS. 7 and 8 situation by reason of the action designated in those figures. Thus in FIGS. 13a to 13d the liquid-filled sections signified by shading may be regarded as lying relatively downstream of the unshaded, gas-filled sections. The latter in the context of FIGS. 13a to 13c may be said to lie relatively upstream in the network.

Similar principles to those described in relation to FIGS. 7, 8 and 13 may be applied to the other embodiments described herein.

FIGS. 9a and 9b show in simplified schematic form an optional alternative basic version of the apparatus in accordance with the invention. In FIGS. 9a and 9b a plurality of volumes 10 are defined inside walled chambers or other structures 11 that may each contain a volume 10.

Each of the volumes 10 includes at least one internal phaseguide 12. The phaseguides may be of the 2D or the 3D type described herein, and are shown as straight lines in the figures purely for purposes of representation.

In FIGS. 9a and 9b the phaseguides 12 are shown spanning the interior of each volume 10 from one side to the other in a straight line. As explained the phaseguides protrude either a short distance into the vertical height of the volume 10 or as a channel in the bulk material in each case (when the phaseguides are of the 3D type) or represent a line of different wettability with respect to the respective bulk material (in the case of both 2D and 3D phaseguides).

The phaseguides could however adopt shapes other than the rectilinear ones shown.

The phaseguides 12 in FIGS. 9a and 9b are confining phaseguides. As explained, such phaseguides are intended to prevent the flow of an advancing liquid, and halt the meniscus along a plane corresponding to the line of the phaseguide.

The structure of FIGS. 9a and 9b is a "second order" network with two levels of branch hierarchy. At the branches of lowest hierarchy, each volume 10 is by way of an inlet conduit 14 in fluid communication with a feeding conduit 13 that is common to a plurality of the volumes 10. At the second hierarchy level, the common feeding conduits are connected to one and the same supply conduit 16 that is in turn connected to a source of a liquid-based substance that is required to fill into the volumes 10.

As illustrated by arrow 17 such a liquid-based substance may be caused to flow along the supply conduit 16 from where it feeds via the feeding conduits 13 and the inlets 14 into the insides of the volumes 10. The menisci of the bodies of liquid that thus enter the volumes advance until they are aligned along the phaseguides 12.

The phaseguides 12 are of the "confining" type as explained herein and in WO2010/086179 A2. Therefore the menisci are not intended to advance beyond the phaseguides unless additional energy is applied. As a result during a filling operation each volume 10 becomes partially filled with (in the embodiment shown) the same quantity of the liquid-based substance, essentially simultaneously. The result of this activity is shown in FIG. 9b.

As is signified by the dotted lines in the arrangements of FIGS. 9a and 9b a large number of the volumes may be connected in a regular or irregular network using the conduits indicated. The ability to fill each of them simultaneously with a desired quantity of the liquid-based substance renders the apparatus of FIGS. 9a and 9b potentially highly useful in various pharmaceutical, chemical and biological testing, experimentation and trailing situations.

In FIGS. 9a and 9b the volumes 10 are shown in an incomplete form. In practice each of them would include a further inlet connected on the opposite side of the illustrated phaseguide in each case to that shown (perhaps connected via a similar network of common feeding conduits to another supply conduit) and at least one vent. The same omissions have also been made, for clarity, from FIGS. 10, 12 and 14.

As phaseguides do not significantly interfere in the transport of a homogeneous liquid or gas fluid, gas outflux is not affected by the phaseguides.

FIGS. 10a to 10c show liquid aliquoting confined on two phaseguides inside the volume 10 in conjunction with an excess flow volume 19.

In this particular set-up at least three vents would need to be present: one to vent the area on the left of the confining phaseguide 12a described below, one on the right of the confining phaseguide 12b and one to vent the excess flow volume 19.

In FIGS. 10a to 10c an inlet 14 which is similar to one of the inlets 51 of FIGS. 7, 8 and 9 connected to a volume 10 includes a side branch 18. The side branch 18 opens into an excess flow volume 19 that in the embodiment shown is a rectangular or cylindrical container (although this need not be so in every case).

The interior of volume 10 is divided by two parallel phaseguides 12a, 12b extending from one side of the parallel-sided volume 10 to the other. The phaseguides 12 extend from one wall of the chamber to the other one on either side of the location at which the inlet 14 opens into the interior of the volume, and are of the confining type. Therefore they define in the volume 10 a volume region 21 that is in the embodiment shown parallel-sided and cuboidal (although other shapes are possible within the scope of the invention).

The side branch 18 includes a further excess flow phaseguide 22 spanning the entrance to the excess flow volume 19. Although the excess flow phaseguide 22 also is of the confining type its stability is less than that of the phaseguides 12 inside the volume 10 or phaseguide 31 in FIGS. 12 and 14 described below.

A process of filling the volume region 21 involves causing a flow of liquid-based substance, represented by arrow 23 in FIGS. 10b and 10c, to pass along inlet 14 (for example through operation of the supply conduit and one of the feeding conduits 13 of FIGS. 7 to 9). During initial filling of the volume region 21 the excess flow phaseguide 22 prevents any fluid from entering the excess flow volume, and instead all the fluid initially enters the volume region 21.

Here the phaseguides 12 constrain the liquid-based substance to adopting the shape and volume of the volume region 21. Once the volume region is full, as illustrated in FIG. 10c, any further flow of the liquid-based substance breaches the excess flow phaseguide 22 which by reason of its lesser stability is more easily breached than the phaseguides 12a and 12b. This causes or permits overflow of any excess liquid into the excess flow volume 19.

This in turn means that filling of a small volume in a microfluidics environment may be achieved very accurately. This is because it is necessary to supply fluid via the inlet 14 only until the fluid starts to enter the volume (reservoir) 19. At this point the researcher has certainty over the error margin in the volume that he is injecting, based on the capacity of the volume 19.

The excess flow volume 19 is positioned in the illustrated example at a branch of the inlet channel. Alternatively, the volume may be positioned downstream from the volume 10 and upstream from a vent. This configuration is described in more detail in WO2010/086179 A2.

As in the case of FIGS. 9a and 9b, FIGS. 10a to 10c omit for clarity the optional second and third inlets and the vents that would normally connect to the volume 10.

Variants on the FIG. 10 arrangement are possible within the scope of the invention.

For example one or both the phaseguides 12 could be replaced by walls of the chamber 11. Moreover the phaseguides could adopt any of a range of shapes and need not both be of the same design.

The excess flow volume 19 moreover typically would include a vent permitting the expulsion of gas in it during the filling activity.

The arrangement of FIGS. 10a to 10c is most suited to a situation in which there is only one of the volumes 10, or in which each volume 10 of a plurality is fed by a separate feeding conduit 14. In the arrangement of FIGS. 7 and 9, on the other hand, in which multiple volumes 10 are fed by common feeding conduits 13 it is more efficient to provide an excess flow volume for a group of the volumes 10.

This arrangement is shown in FIGS. 11a to 11c.

FIGS. 11a to 11c show an arrangement that is a hybrid of FIGS. 9 and 10. Since the apparatus of FIGS. 9a and 9b includes a number of the volumes 10 connected by the supply conduit 16 and several of the common feeding conduits 13 it is not necessary to locate an excess flow volume in the inlet 14 to each of the volumes 10. On the contrary in FIGS. 11a to 11c there is provided a single excess flow volume 19 branched from the supply conduit 16.

An excess flow phaseguide 22 exists in the branch leading to the excess flow volume (reservoir) 19. As in the case of the FIGS. 10a to 10c embodiment, the stability of the excess flow phaseguide 22 is less than that of the phaseguides 12 located inside the volumes 10. In consequence during filling the volumes 10 all fill with a liquid-based substance before the liquid-based substance becomes able to flow over the excess flow phaseguide 22. Further in consequence this means that all the volumes 10 are filled with a desired aliquot of the liquid-based substance before any flow into the excess flow volume occurs.

FIGS. 11a to 11c, like FIGS. 10a to 10c, show a sequence of filling the volumes 10.

The excess flow volume 19 does not need to be located as shown, "upstream" of the network of volumes 10. On the contrary the reservoir 19 may lie at any chosen location where it may come in contact with the liquid based substance during filling.

Phaseguides that control a filling process, such as the phaseguides 22 in FIGS. 10 and 11 may be patterned repetitively such that the system continues to function correctly even in the case of unintended breaching of one or more of the repetitive phaseguides.

Also the variants on the arrangements described above in relation to FIGS. 10a to 10c are applicable in the FIGS. 11a to 11c embodiment, following further modification as necessary.

FIGS. 12a to 12c show a similar arrangement to that of FIGS. 10a to 10c, with the modifications that the excess flow volume 19 is not present; and an additional confining phaseguide 24 exists in the inlet 14, over and above a phaseguide 31 which may be referred to as a "metering phaseguide" in the side branch 18.

The method of filling the volumes 10 in the FIGS. 12a to 12c is shown in sequence. Starting from an empty volume 10 the liquid-based substance 26 is caused or permitted to flow into the volume 10 thereby filling the volume region 21 between confining phaseguides 12 that for convenience are shown in the same orientation as the counterpart phaseguides in FIG. 10 but could of course be arranged differently.

Additional phaseguide 24 is of lower forward stability than excess metering phaseguide 31. As a result during filling as signified by arrow 27 in FIG. 12b the meniscus of the liquid-based substance 26 breaches phaseguide 24 and flows over it to fill the volume region 21.

Depending on the design criteria adopted, metering phaseguide 31 might or might not be of lower forward stability than phaseguides 12 and the conduit 18 might or might not be used as an excess flow volume.

The metering phaseguides 31 may be constructed in accordance with principles explained herein to be anisotropic so that a different stability value applies depending on the sign of the applied pressure (forward or reverse) over the confined meniscus.

Taking advantage of this possibility the liquid flow in inlet 14 may subsequently be reversed, as indicated by arrow 28 in FIG. 12c. In this case the stability of the metering phaseguide 31 in the "reverse" flow direction may be arranged to be less than that of phaseguides 12 when the flow is as signified by arrow 28. As a result the pinning of the meniscus of the body of liquid on metering phaseguide 31 is breached and the branch 18 and most of the inlet 14 become vacated. Subsequently the meniscus is cut into two along phaseguide 24. As a consequence the aliquot of liquid-based substance in the volume region 21 is separated from the bulk liquid and precisely metered.

In an alternative to the FIG. 12 arrangement the cross-sectional area of the inlet 14 may be made smaller than that of the side branch 18. This means that the phaseguide 24 potentially may be omitted while providing for a similar metering function to that described.

The side branch 18 of FIGS. 12a to 12c could be connected to a reservoir such as reservoir 19 of FIGS. 10 and 11, or it may attach to a gas exhaust via which gas (typically but not necessarily air) may flow in the conduits when liquid direction is reversed and liquid is metered.

When both the metering structure and the excess flow volume are connected to the network it is normally desirable that the metering phaseguide 31 is of higher forward stability, but of lower reverse stability, than the excess flow phaseguide 22.

FIGS. 13a to 13d show an extension of the principle of FIGS. 12a to 12c to an apparatus of the general kind shown in FIGS. 7a to 7d, in which multiple volumes 10 are present.

The FIG. 13 embodiment is similar therefore to the FIG. 7/FIG. 8 arrangement, with a small addition/modification such that it can also be used to isolate liquids from one another. In this case, the phaseguide $63^n$ guarding the volume 10 that is positioned along the common feeding conduit 13 furthest from the point of emptying adopts the function of phaseguide 31 in FIGS. 12a to 12c and is of lower stability than the other phaseguides $63^1$, $63^2$, etc of the volumes connected to the same common feeding conduit 13 that lie closer to the point of emptying.

The common venting conduit 53 may or may not be filled with liquid.

The volume 10 along the common feeding conduit 13 that is furthest from the point of emptying will not contain isolated liquid after the operation. In fact, that specific volume may well be of no interest to the user and may be, or may act as, a channel.

Furthermore, the common venting conduit 53 is not mandatory.

The apparatus in FIGS. 13a to 13c may be part of a higher order network that has multiple branch hierarchies. In a configuration in which all branches are envisioned to be emptied, except for the branch that is lowest in hierarchy and contains the volumes that are to be isolated, the configuration is similar to the configuration of a higher order network of FIG. 8, except for the branch that is lowest in hierarchy, which contains the structure of e.g. FIG. 13a. For a correct functioning of the network the phaseguide $63^n$ of the branch that is lowest in hierarchy needs to be of lower stability (in the reverse direction, with respect to the receding liquid meniscus) than the phaseguide $63^n$ that is of lowest stability in a branch of higher hierarchy.

FIGS. 14a to 14c show an extension of the principle of FIGS. 12a to 12c to an apparatus of the general kind shown in FIGS. 9a and 9b, in which multiple volumes 10 are present.

The FIG. 14 embodiment is similar therefore to the second order arrangement of FIG. 9, except that each of the common feeding conduits 13 has a metering phaseguide 31 and phaseguides $12^1 \ldots 12^n$ at the higher hierarchy level of the branching network. The aim is to provide multiple metered aliquots in the volumes 10.

At its end remote from the supply conduit 16 each common feeding conduit 13 is connected to a vent of the general kind described herein. The connection to the vent includes a respective metering phaseguide 31 the stability of which is chosen to assure correct, accurate filling of all the volumes 10 before breaching (if any) of any metering phaseguide 31 occurs.

The filling situation, represented by arrow 32, is shown in FIG. 14*a*.

Emptying of the common feeding conduits 13 occurs by way of reversal of the flow direction, indicated by arrow 33 (FIG. 14*b*). As in the FIG. 13 arrangement, the reverse flow stability of the phaseguides 12 at the higher hierarchy level is higher than that of the metering phaseguides 31 in order to assure emptying of each common feeding conduit before breaching any of phaseguides $12^1$, $12^2$, etc of the next-highest hierarchy level takes place.

Moreover, the reverse flow stability of the metering phaseguides 31 is lower than any of the phaseguides 12 such that each aliquoted volume remains pinned on a phaseguide 12, while liquid is metered.

Emptying of the conduits 16 (if required), occurs according to the scheme of FIG. 8, following emptying of all the conduits 13. The stabilities of phaseguides 12 when considering flow in the emptying direction assure that breaching of phaseguides 12 occurs in the order commencing with of the phaseguide 12 furthest from a source to which supply conduit 16 is connected.

As the cross-sectional area of the inlet 14 is in this example smaller than that of the conduit 13, the liquid is cut by the receding meniscus and liquid 10 is thus separated from the bulk liquid resulting in metering of the aliquots in volumes 10.

As an alternative to metering by using the narrow cross-section described an additional confined metering phaseguide may be patterned at the entrance of each volume 10. This phaseguide will define the metered liquid border in a similar way to phaseguide 24 in FIGS. 12*a* to 12*c*.

The phaseguides 12 and 31 in e.g. the FIGS. 12 and 14 are defined both in terms of their forward and reverse stability. FIGS. 15*a* to 15*c* show three preferable phaseguide arrangements to provide this.

FIG. 15*a* employs a triangular phaseguide 12*a*, in which each side of the phaseguide has an angle, a with the wall of the channel. In FIG. 15*a* the angle $\alpha_{adv}$ refers to the angle $\alpha$ influencing phaseguide stability when considering forward stability (i.e. corresponding to advancing of the meniscus); and $\alpha_{rec}$ the angle $\alpha$ of relevance to reverse stability (corresponding to meniscus recession).

In FIG. 15*b*, the stability of a branch-type phaseguide 12*b* is tuned by the angles $\alpha_{adv}$ and $\alpha_{rec}$ of the branches in both directions; and in FIG. 15*c*, the stability is tuned by the angles $\alpha_{adv}$ and $\alpha_{rec}$ of a V-shaped phaseguide 12*c*. In each of FIGS. 15*b* and 15*c* the angles $\alpha_{adv}$ and $\alpha_{rec}$ may be construed similarly to their meanings in FIG. 15*a*.

The phaseguide arrangement of FIG. 15*a* has an advantage over those of FIGS. 15*b* and 15*c* that alignment of the phaseguide arrangement in the x- and y-direction with respect to the channel wall 59 is less critical. The arrangements of FIGS. 15*b* and 15*c* have the advantage over the FIG. 15*a* embodiment that alignment in terms of the rotational angle is less critical.

FIGS. 16*a* to 16*c* illustrate an arrangement in which one of the volumes 10 is internally divided by a confining phaseguide 12 into first and second parts 10*a*, 10*b*.

Phaseguide 12 spans the width of the volume 10 as shown, although other shapes and arrangements of the phaseguide are possible.

The volume 10 includes a contour phaseguide 34 defining a venting region adjacent the confining phaseguide, with one inlet 14' connecting to the first part of the volume on one side of the confining/contour phaseguide pair and another inlet 14" connecting to the second part of the volume on the other side of the confining/contour phaseguide pair. The venting region 36 is defined in the embodiment shown as an elongated strip spanning the volume 10 in a location between entry points of the inlets 14', 14".

The contour phaseguide 34 includes an engineered overflow point 37 at the end of the venting region 36 that lies remote from the inlets 14', 14". As a result breaching of the phaseguide 34 occurs at this remote end and the venting region fills therefrom.

The engineered overflow 37 is here schematically depicted as a reduced phaseguide wall angle. It may however be any type of configuration that enforces overflow at that specific location along the phaseguide, including but not limited to a branch, inlet or V-bend.

A venting conduit 52 permits fluid to vent from the venting region during filling of the part 10*b* of the volume 10.

The venting conduit 52 contains a further phaseguide 63 and the inlet 14' contains a confining phaseguide 24.

The process of operating the volume 10 of FIGS. 16*a* to 16*c* involves firstly causing a first liquid-based substance 26*a* to fill the left hand part 10*a* of volume 10 via inlet 14'. The confining phaseguide 12 prevents the aliquot in part 10*a* from spreading into part 10*b* of volume 10. The liquid is subsequently metered and confined by confining phaseguide 24. This is illustrated in FIG. 16*a*.

Subsequently, as shown in FIG. 16*b*, the right hand part 10*b* of volume 10 is filled, typically with a different liquid-based substance 26*b*, via inlet 14".

The contour phaseguide 34 causes the substance 26*b* to fill towards the overflow point, and only when volume region 10*b* is completely filled with liquid-based substance 26*b* is phaseguide 34 overrun by liquid based substance 26*b* at this overflow point 37 (FIG. 16*c*). When this happens the substance 26*b* starts to fill venting region 36, expelling any gas (typically but not necessarily air) in it via the venting conduit 52.

At this point the two liquid-based substances 26*a*, 26*b* contact one another and are further confined by phaseguide 63.

In FIGS. 16*a* to 16*c* only liquid 26*b* overflows the phaseguide 37. Upon reaching phaseguide 12 liquid 26*a* is contacted from the opposite side by liquid 26*b* and phaseguide overflow occurs at the moment of contact, as the contact relieves the pinning.

In this manner two liquids can be brought into contact, largely without disturbing the liquid profile of either of the quanta of liquid 26*a*, 26*b*. The distance between the two phaseguides 12, 34, the positions of the venting region 36 and phaseguide 63 and the point of overflow of phaseguide 34 between them determine the extent to which the fluid profile is distorted during the filling process.

As in the case of other embodiments of the invention the extremities of the volume 10 may be bounded by chamber walls, further phaseguides or combinations of such components. Phaseguides 63 and 24 may however be absent. A network, as in e.g. the FIGS. 9*a* and 9*b* embodiment, containing large numbers of the volumes 10 may be provided for example in order to run many chemical or biological assays in parallel using the apparatus of the invention.

Furthermore the structure of the two phaseguides 12 and 37, the inlet 14" and the vent 52 may be repeated for facilitating the insertion of multiple liquids. The basic structure would be repeated (n−1) times for inserting n liquids in the volume 10.

One or more of the excess flow volumes 19 shown in FIGS. 10a to 10c moreover may be added at chosen locations along the feeding and supply conduits that may be connected to the FIG. 12 apparatus in order to supply the liquid-based substances.

When such an excess flow volume is present, the phaseguide 63 needs to be of higher stability than the excess flow phaseguide 22 in FIGS. 10a to 10c. This allows precise aliquoting of the second liquid 26b and minimal distortion of the liquid profile once the two liquids 26a and 26b are connected and the venting region 36 is filled.

Furthermore the structure may be coupled with the metering structure of FIGS. 12 and 14. In this case metering phaseguide 31 in FIG. 14 needs to be of lower stability in reverse flow than phaseguide 63.

FIGS. 17a to 17e are direct counterparts of FIGS. 16a to 16c, with the difference that (as shown) the phaseguides 12' and 34' are shaped to provide a non-rectilinear venting region 36'.

Such an arrangement, which functions essentially in the manner described above with reference to FIGS. 16a to 16c, leads to a larger contact area between the liquid-based substances 26a, 26b and thus causing a faster exchange of compounds contained by the substances due to diffusion. The FIG. 17 embodiment therefore may be of particular use when studying e.g. a reaction (such as but not limited to a catalysis or assay reaction) in which the intimacy of mixing of ingredients is important.

FIGS. 18a to 18c illustrate another embodiment of the invention in which a first liquid-based substance 26a is confined on one, first side 10a of a confining phaseguide 12 inside a volume 10. This occurs as a result of the presence of confining phaseguide 12 together with an additional confining phaseguide 24 located in a first inlet 14' communicating with the first side 10a of the volume 10.

A further liquid-based substance 26b introduced via a further inlet 14" on the part 10b of the volume 10 defined on the opposite, second side of the confining phaseguide 12 can be brought into contact with the first liquid-based substance upon reaching the confining phaseguide 12.

This effect relies on the principle that if a meniscus that is confined by a phaseguide is contacted from the opposite side, phaseguide overflow occurs at the moment of contact as the contact relieves the pinning.

A vent 5252 communicates with the volume part 10b to permit expulsion of substances from the volume parts 10a and 10b during filling of each of the liquid-based substances 26a, 26b. The vent is closed by a phaseguide 63.

Furthermore one or more of the excess flow volumes 19 shown in e.g. FIGS. 10a to 10c may be added at chosen locations along the feeding and supply conduits that may be connected to the FIG. 10 apparatus in order to supply the liquid-based substances.

In the case of an excess flow volume 19, phaseguide 63 would be of higher stability than the excess flow phaseguide 31 in FIGS. 10a to 10c, thus allowing precise aliquoting of the second liquid 26b.

Furthermore the structure of the two phaseguides 12 and 24 and the inlet 14' may be repeated for facilitating the insertion of multiple liquids. The structure would be needed (n−1) times for inserting n liquids in the volume 10. The vent 5252 is needed only once for inserting n liquids. However the vent 5252 needs to be positioned such that it facilitates venting of liquid or gas up to the last filled liquid n.

FIGS. 22a to 22c show a similar embodiment of the invention as in FIGS. 16a to 16c that may be used in a method of selective recovery of liquid from the volume 10. In this case the volume 10 is divided into two dominant liquid volume parts 10a, 10b that are separated by two phaseguides 12, 34 in close proximity to one another and defining a venting region 36.

A venting conduit 5252 is connected to venting region 36 and is guarded by a confining liquid phaseguide 63. A respective inlet 14', 14" is connected to the interior of each of the volume parts 10a, 10b. The two inlets 14', 14" include confining phaseguides 24', 24".

The phaseguide 34 may include an engineered overflow point 37 at its end remote from inlet 14".

In its initial condition (FIG. 22a) the two parts 10a, 10b and the venting region 36 are filled with respective liquids 26a, 26b. The application of gas pressure via conduit 52 or a reduction in pressure at inlet 14" forces the liquid meniscus 26 to recede starting from phaseguide 63. Meniscus pinning by the phaseguides 12, 34 and the operation of the reduced-stability portion 37 means that the liquid preferentially is expelled first from the venting region 36 followed by volume part 10b via inlet 14", and at this stage (FIG. 22b) no liquid is expelled from part 10a.

Phaseguide 63 is of lower reverse stability than phaseguide 24', such that meniscus retraction occurs at phaseguide 63 upon application of a negative pressure via inlet/outlet 14". Thus the space between the two phaseguides 12, 34 fills with air/gas separating liquid 26a from liquid 26b. As shown in FIG. 22c the isolated liquid 26a may then be fully recovered separately from liquid 26a.

The FIG. 22 embodiment also works in the case that a positive pressure is applied to conduit 52. If phaseguides 63 and 34 are of lower reverse stability than phaseguide 24', overflow of phaseguide 24" will occur and the space between phaseguides 12 and 37 will be filled with air to separate the two liquids. Subsequently, overflow occurs at phaseguide 34 and liquid 26b is further repelled from volume 10b.

Yet a further variant is illustrated in FIGS. 23a to 23c.

Constructionally FIGS. 23a to 23c show a similar arrangement to FIGS. 22a to 22c, but the phaseguide stabilities are again chosen to produce a specific, and different, mode of operation.

More particularly the stability of phaseguide 24' in FIGS. 23a to 23c is less than that of phaseguides 63. Therefore on the application of a negative pressure via inlet 14" meniscus retraction commences from phaseguide 24' as shown in FIG. 23b.

Assuming the stabilities of the phaseguides 12 and 34 are less than that of phaseguide 63 the volume parts 10a and 10b and the venting region will empty in the order apparent from FIGS. 23b to 23c.

In each of the examples of FIGS. 22 and 23 a volume 10 divided into two parts 10a, 10b is shown. It is however possible within the scope of the invention to sub-divide a volume such as volume 10 into more parts, thereby permitting processing of more than two liquid-based substances as desired.

In a general case, a liquid is divided into partitions by phaseguides 12 or 34 and each partition is communicating with a conduit (5252 or 14) that contains a phaseguide 24 or 63. Upon application of suction at an inlet, the partitions of liquid that are expelled are defined by the confining phaseguide 14 or 63 that is of lowest stability.

In a second general approach, upon application of a positive pressure to one of the conduits 5252 or 14, the partitions of liquid that are expelled are defined by the phaseguide 24 or 63 of lowest stability.

In both cases, the expelled liquid comprises by approximation the liquid portion in communication with the conduit to which pressure (positive or negative) is applied and the liquid portion in communication with the phaseguide of lowest stability, as well as all liquid portions in between of these two liquid portions.

In any of the embodiments described one or more supporting or dead-angle phaseguides may be present for the purpose of guiding the flow of liquid-based substances according to desired patterns, routes and shapes and assuring a complete filling of the extremes of the volumes (i.e. dead angles). It is important though that these supporting and dead angle phaseguides are of lower stability with respect to an eventual excess flow and/or confining phaseguide.

As explained in WO2010/086179 A2, the filling of dead angles (i.e. corners and apices of the geometry that might otherwise be hard to fill completely) may be made much more reliable through the use of dead angle phaseguides that promote complete filling of such spaces.

Also the phaseguide pattern inside the chamber may adopt a wide variety of forms, including various patterns for (confined) aliquoting, dead angle and supporting phaseguides and the positioning of any additional type of confining phaseguide.

Forward Flow During Filling

In the invention confining phaseguides determining the amount of aliquoted liquid-based substance in the volume (phaseguides 12 in the FIGS. 7 to 23) are the most stable phaseguides encountered by a liquid-based substance that is filling a volume or a plurality of volumes. Under forward flow conditions, these confining phaseguides are not intended to be overrun unless contacted from the opposite side by a second liquid-based substance.

The venting phaseguide inside or downstream from the volume is also a confining phaseguide, for which the same rules apply as the confining phaseguides 12 in forward flow.

Supporting and control phaseguides, such as the ones adjacent the supply conduit for multiple volume metering, are typically of lowest forward stability. This is also true for the confined metering phaseguide that determines the meniscus position after metering. The relative stability amongst these three types of phaseguides is of minor importance in the invention.

The stability of the excess flow phaseguide is such that it is flowed over or breached once all parts of the network are filled. This means that under forward flow conditions the excess flow phaseguide is less stable than the confining phaseguides 12, but more stable than the supporting, control and confined metering phaseguide.

This same applies to a metering phaseguide whereas for the case of both a metering phaseguide and an excess flow phaseguide in the network to be filled by one liquid, the excess flow phaseguide is of lower stability than the metering phaseguide under forward flow.

Reverse Flow During Metering

If flow is inverted during metering, it is crucial that the metering phaseguide is flowed over first. Therefore, this phaseguide needs to be of lower stability than any phaseguide by means of which liquid-based substance is contemporaneously confined, these being typically confining and venting phaseguides. The metering phaseguide needs also to be of lower reverse flow stability than any excess flow phaseguides, in the case that both are available. It is clear again that the excess flow and metering phaseguides may be the same. It is also clear that when liquid-based substance has merged with a further liquid-based substance during a preceding step, the stability of the phaseguides by which this further liquid-based substance is confined becomes of similar importance.

The control phaseguides such as the ones $12^1$, $12^2$, etc adjacent to the supply conduit 16 in FIGS. 14a to 14e need to be of higher reverse flow stability than the metering phaseguides, in order to assure emptying of all common feeding conduits and thus metering of all the connected volumes.

When it is required to empty the supply conduit 16, it is important that the control phaseguides are of lower stability than the excess flow phaseguide. Also, as discussed above, control phaseguides need to be of increasing stability with respect to one another, depending on their distance to the feeding source, the least stable phaseguide being the one furthest away from the source.

Reverse Flow During Recovery/Emptying

For a system with multiple inlets and vents the order of phaseguide overflow is essential to recover a complete or a selected part of a liquid-based substance from the volume. Considering that a liquid based substance is confined on all sides on a phaseguide, the phaseguide that is intended to be flowed over should be of lower stability than the other confining phaseguides. As it is probable that the meniscus during retraction will encounter various supporting, dead-angle, confining and contour phaseguides, the stabilities of these phaseguides need to be carefully chosen with respect to the stability of the confining phaseguides and the required emptying approach.

For instance, if a structure such as the one in FIG. 18 needs to be emptied, e.g. by applying a negative pressure at inlet 14", an additional venting phaseguide needs to be added to block vent 52. It may be preferred to have phaseguide 24 flowed over first followed by emptying of area or volume 26a, and overflow of phaseguide 12 (which needs to be of lower reverse stability than this additional venting phaseguide (not drawn)). It may be arranged that phaseguide 12 is flowed over at the top of the chamber, distant from inlet 14", in order to empty the complete volume 26b. It may also be chosen to add additional supporting and dead-angle phaseguides, to ensure complete emptying of volumes 26a and 26b. These phaseguides need then to be always of lower reverse flow stability than the additional venting phaseguide.

A different method of emptying this chamber could include applying a positive pressure at for instance inlet 14'. For the case that both inlet 14" and vent 52 contain a confining (venting or confined metering) phaseguide, overflow of one of these two phaseguides is determined by their relative stability.

A similar, more complex scheme has been described for FIG. 22 (selective partial recovery) and FIG. 23 (complete recovery).

The various embodiments described in the above figures give rise to a typical method for processing liquids in the device. A first liquid is inserted into one or a plurality of volumes. This liquid is confined by a phaseguide 12 or 63 and upon inserting more than that volume, an excess flow phaseguide is breached and excess flow fills the excess flow volume. Upon filling of the desired volume region or after breaching the excess flow volume the fluid flow is reversed, such that the metering phaseguide is breached and the liquid meniscus is separated into two. The aliquoted and metered liquid in the volume region is preferably pinned on both confining phaseguides 12 or 63 and confining phaseguide 24.

A second liquid is optionally inserted following largely the same procedure. In the case of a liquid aliquoting structure as described in FIG. 18, the second liquid based substance is merged with the first liquid based substance followed by confinement by the venting phaseguide 63 and confining phaseguides 24. In the case of structures such as in FIGS. 16 and 17, the second liquid based substance fills up the second volume region 10b, followed by breaching of the contour phaseguide 37, subsequent merging with liquid based substance 10a and confinement on the venting phaseguide 63. A second excess flow phaseguide is breached upon addition of an excess of flow-based substance volume, after which the flow is reversed and the two merged liquid based substances are metered.

Optionally additional liquids may be inserted following the same method or a variation on this method.

After processing of the liquid based substances, the processed liquid based substance may be partly or fully recovered as outlined above.

FIG. 19 illustrates an arrangement for routing of liquid-based substances in accordance with the invention in which two liquid-based substances 26a, 26b are routed to multiple volumes, filling the respective volume parts 10a, 10b of a network of volumes 10 and a third liquid-based substance 26c is inserted individually into each volume 10. The volumes are of the same basic construction as those shown in the preceding embodiments.

The composition of the liquid-based substance 26c injected into each volume 10 does not need to be the same in each case; and indeed all the substances 26c may differ from one another.

The respective parts 10a, 10b, 10c of each volume are defined by liquid insertion arrangements such as shown in FIGS. 16, 17 and 18 (that in the embodiment shown simply result in the stripe-like appearance shown but that in other embodiments of the invention may take other forms). The volumes and or the network may further comprise a liquid metering and/or excess flow embodiment, such as described in FIGS. 10, 11, 12 and 14.

The order in which the liquid-based substances 26a, 26b, 26c are arranged is in this case not of importance and can be altered. Also the sequence of injection can be chosen depending on the chosen phaseguide pattern and positioning of the vent.

Common feeding conduits 13 are connected as appropriate in order to provide for delivery of the liquid-based substances 26a, 26b, 26c. The vents are omitted from FIG. 19 for clarity of illustration.

The routing scheme of FIG. 19 could be expanded by the addition of more liquid-based substances that are individually inserted, similarly to liquid based substance 26c. Also, it is not required that both common feeding conduits address all volumes in the array, or that both common feeding conduits address the same volumes.

However, it is not possible to address more than two volumes with more than two common feeding conduits, without needing additional microfluidic layers to allow for crossing of microfluidic channels.

FIG. 20 shows an embodiment that is similar to the FIG. 19 embodiment, except that instead of utilising the individual injection of the third liquid-based substance 26c this liquid-based substance is routed through a common feed. As a result all the quanta of the third substance 26c are injected simultaneously instead of individually as in the FIG. 19 example.

A consequence of addressing multiple volumes 10 by more than two common liquid conduits is that conduits need to cross each other, without bringing the respective contained liquids in to contact with each other. Therefore fluidic vias 38, three of which in FIG. 20 are labelled and plural examples of which are visible in the figure, are necessary. A via connects a fluidic network on one plane with a fluidic network on a second plane that may or may not be at the same level (height) as the first plane. The two fluidic planes are separated from one another by at least one layer of material. A via typically consists of a hole or channel through this material connecting one channel or conduit in one layer to a second channel or conduit in a second layer.

FIG. 21 shows a more complex routing network in which a liquid-based sample 26a is distributed over three of the volumes 10. In addition, three liquid-based reagents 26b, 26c, 26d are dispensed in various combinations in the volumes 10, in dependence on the routing network.

The method of using the FIG. 21 apparatus is referred to herein as "combinatorial microfluidics". Combinatorial microfluidics gives full flexibility in combining liquid-based substances as well as to the respective volumes to be combined.

The invention is suitable to permit aliquoting of multiple liquids, one next to the other, for controlled reactions in well defined volumes. Combination with the above-described multiple aliquoting idea would result in combinatorial microfluidics techniques in which reagents and samples can be screened in any pre-defined combination and quantity.

The invention is particularly useful for massive parallel screening and synthesis. Advantages of the invention lie in the reduction of pipetting steps due to partial automation of dispensing and fluidic routing steps. The invention can be used for extremely small volumes and allows one-step massive parallel assaying of sample or reagent aliquots. The invention further allows extremely precise metering of liquids and has the advantage over microtiter and multiwell plates that the closed volume approach limits evaporation and allows precise control over parameters such as diffusion and heat transport. Another unique aspect of the invention is that screening or reaction products can be partly or completely recovered for further analysis.

Applications that can be implemented include all applications that are normally executed in multiwell or microtiter plates. In addition, the platform allows a number of processes that cannot be performed on these plates. Samples under test can be any type of fluid, including suspensions (e.g. cell suspensions or bead suspensions), emulsions, fluids with dissolved compounds, fluids with non dissolved compounds (e.g. lipoproteins) or pure fluids. Fluids may contain biomolecules, cells organelles, particles, beads, organisms (e.g. zebrafish or embryos) and/or vesicles. The fluids may be simple, e.g. water; or highly complicated such as blood and other body fluids, waste- and drinking water, foodstuffs and other materials/mixtures.

Assays based on nucleic acid based amplification techniques, such as PCR including real-time PCR and digital PCR, NASBA, LAMP (Loop Mediated Isothermal Amplification), rolling circle amplification, Helicase dependent isothermal amplification and RPA (Recombinase Polymerase Amplification) can be easily be performed using embodiments of the disclosed invention.

The following is an example of use of the FIG. 19 arrangement and may be taken together with the other examples to follow:

The FIG. 19 arrangement could be beneficial when a sample under test (in this case substance 26b) needs to be incubated first with one reagent (i.e. substance 26a) followed by reagent addition (substance 26c) and further incubation and readout of the assay.

An example of such an assay is a real-time NASBA (Nucleic Acid Sequence Based Amplification) assay. Such an assay requires precise, constant temperature control. In NASBA, incubation at a high initial temperature, typically 65° C., is needed for one reagent mixture (e.g. substance 26a) and sample (e.g. substance 26b) in order to unfold secondary RNA structures.

After cooling typically to 41° C., an enzyme mix (i.e. substance 26c) is added and the amplification process is started at this lower temperature.

The embodiment facilitates a fast heat transfer through the chamber walls and, if real-time readout of the amplification process is required, an optical, typically fluorescent, readout can be facilitated.

An advantage of an embodiment such as that shown in FIG. 19 for such a NASBA reaction is that samples and reagents can be inserted in precise quantities.

The number of pipetting steps needed for running this assay is (n+2), where n is the number of samples, plus two reagent addition steps. A typical prior art NASBA assay on the other hand requires 3*n pipetting steps, as normally the two reagent addition steps need to be executed for every sample well.

A further advantage of the FIG. 19 method is that the process can be easily automated e.g. in a robot-controlled rig or sampling station.

In such arrangements the pattern of inlets of each conduit depicted by the arrows in FIG. 19 can be arranged to match the layout of the wells in a titre plate.

The following is an example of use of the FIG. 20 arrangement for processing a real-time PCR assay:

An example of use of such an embodiment may arise in a parallel real-time polymerase chain reaction (PCR) run. A dilution series of a liquid-based sample 26a may be introduced in the volumes 10 in differing volumes and subsequently become diluted with e.g. water 26b. Then PCR reagent solution 26c is added and a PCR run commenced.

This represents an extremely fast and simple method for preparing a real-time PCR run, saving numerous pipetting steps.

In both examples the embodiment needs to facilitate a fast heat transfer through the chamber walls and, if real-time readout of an amplification process is required, an optical, typically fluorescent, readout would be provided.

The embodiment of FIGS. 7 and 13 may be used for digital PCR in which a sample is distributed over a large array of chambers that are subsequently isolated from one another.

Nucleic acid-based amplification is also used for proximity ligation assays in proteomics. This technique can also be implemented using the invention.

The following is an example of use of the FIG. 21 arrangement for combinatorial drug screening:

The concept of combinatorial microfluidics can be used in e.g. combinatorial drug screening, in which for example liquids 26b, 26c and 26d may be pharmacoactive compounds and liquid 26a may be or may convey e.g. a cell sample. An additional liquid may be added containing e.g. a fluorescent marker (not shown in FIG. 21), to determine the effect of the reagent combination on the cell sample.

Clearly the complexity increases significantly with the number of reagents to be combined and the quantity of combined reagents per test.

If a standard 96 well-plate format is used, in which one sample is screened on 95 reagents in combinations of two and in which no two combinations are from the same compound, one would need $$C_2^{95} = \binom{95}{2} = \frac{95!}{2!(95-2)!} = 4465$$

screening chambers.

If it is desired to test in combinations of three reagents, the number of chambers required is 138 415. Similar calculations can be made for 384 and 1536 well plates. The apparatus of invention thus enables parallel screening experiments of massive quantities and requires only a limited amount of pipetting steps.

The examples below describe applications of the invention in various combinations of the described components and parts.

Classical immunoassays such as ELISA can also be performed using variants of the embodiments of the invention. A standard indirect ELISA consists of an antigen immobilization step, a non-specific blocking step, addition of a primary antibody and a secondary antibody and finally addition of a substrate that reacts with the enzyme-linked secondary antibody.

The immobilization step can be performed either on the material of the device or on a small carrier, such as beads. The immunoassay requires a number of washing steps, which is typically done through flushing with reagent. This can be done in roughly two ways. The first is a continuous flow flushing system, in which the reagent is simply changed. A second manner is to remove a first reagent from the chamber, such that it is empty again except for the immobilized substance. In a subsequent step a flushing liquid or a next reagent may be added.

Another way of implementing washing steps is to use externally actuatable microparticles (e.g. beads) to which part of the assay, typically the antigen of interest or the antibody, is attached. Once the bead suspension is inserted into a volume, the beads can be transported from one liquid into a bordering liquid, thus realizing washing and reagent addition steps.

For instance an antibody immobilized onto the surface of a magnetic bead can be inserted into a volume in accordance with the invention. If adjacent additional reagent volumes are patterned by the phaseguides, and contain a sample containing the antigen, a secondary antibody containing the reporter and a clean solution representing the wash step, the (magnetic) bead can be sequentially transported from one liquid phase into a next in order to execute an immunoassay.

Cell assays are another important category of method that can be performed using the apparatuses and method steps of the invention. Cell samples can be inserted as cell suspensions or as single cells, depending also on the geometry of the system and the concentration of cells in the starting volume. Cells may also be suspended in a liquid that gelates in order to facilitate culturing in a three dimensional setting.

Cell morphology can be studied upon being brought into contact with reagents, drugs, penicillin and other substances. Also, cell division behavior, cell-cell interaction and fluorescent or luminescent behaviour can be monitored. Tissues can be simulated by inserting multiple cell types in exact quantities and ratios.

Responses to stimuli or challenge tests can be executed in the chambers and the reactions of a single cell, multiple cells, tissues or one or more organisms can be observed once, several times or continuously. Observation can take place either inside the chamber or after recovering (part of) the volume. Many detection techniques can be integrated or used for downstream analysis (see below).

The device may also be used for in-vitro fertilization, with one volume part containing an egg-cell and another sperm cells. Preselection of sperm can be done to assure fertilization with the most healthy and active sperm cell. Also post selection of the fertilized egg cells could be done, e.g. by observation of cell division biochemical tests (sequencing, assaying). Subsequently the most promising experiments can be recovered for further processing or implantation.

The device can also be used for transfection experiments, including gene knock-down/knock-out and genetic modification.

Sequencing experiments, such as pyrosequencing and various "next-generation" sequencing techniques can be also performed using the devices of the invention. Such experiments typically incorporate the addition of nucleotides followed by washing steps. This means that the target molecules need to be immobilized in some way in the chamber. Possibilities for this are bead immobilization or immobilization on the surface (e.g. as arrays).

Also the above-mentioned methodology could be used by immobilizing a sequencing target on magnetic beads that can be transported up and down through solutions with nucleotides and a washing buffer.

The system is also extremely useful for synthesis of compounds. Combinatorial microfluidics allows setting up of large arrays of chambers for testing various reactant combinations, volume ratios, and reagent addition sequences, leading to an extremely high number of reaction products that can be, if required, extracted for further downstream analysis. This may also be used e.g. for screening catalyst activity and effectivity. This will be particularly of advantage for costly compounds, such as many catalysts and enzymes. Also oligonucleotide synthesis or peptide synthesis can be implemented.

Detection techniques that can be employed for analysis inside the chamber include fluorescence microscopy, UV spectroscopy, Surface Plasmon Resonance, Raman spectroscopy, amperometry, potentiometry, voltametry, coulometry, NMR, interferometry and others. Readout of an assay can be done using chemiluminescence and fluorescence means, spectrophotometry (e.g. UV absorption detection) or optical readout through refractive index or colour change. Observation of cell outgrowth, cell division or cell death can be done using phasecontrast microscopy, while confocal microscopy may be used to image affinity markers at specific planes in a cell or tissue.

When further analysis outside of the invention volume is to take place, numerous detection instruments are available, including mass spectrometry, liquid chromatography, gas chromatography, NMR, electrochemical detection and many others.

Mass spectrometry is particularly useful for measuring biochemical profiles. For instance, the excretion of small molecules from a cell or cells in the chamber could be analyzed by recovering part of the volume, not being the cell or cells itself/themselves.

The techniques according to the invention may also be employed in executing electrophoresis experiments, isoelectric focusing, isotachophoresis, blotting or liquid chromatography. In this case a precisely defined sample plug is inserted between two or more electrolyte volumes (being homogeneous, leading/trailing or a gradient) before starting a separation experiment. One or more sample plugs may also be precisely recovered after separation. These experiments may or may not involve gels.

It is clear that for many of the above techniques, the chamber needs to incorporate actuation or sensing electrodes, SPR islands and others. Also the chamber may include elements for guiding an optical path, such as prisms, gratings, waveguides and others.

Electrodes may also be used for end-point detection to control complete filling of structures by measuring capacitance or conduction. End-point detection may also be implemented by inserting a compound that changes colour upon wetting. Filling of the chambers may also be directly observed using a machine vision setup. Chamber filling observation may be based on a change in refractive index, colour or light intensity. Also a marker (e.g. a fluorescent marker) may be added to the liquid in order to facilitate detection of filling or emptying status or progress.

Evaporation may be a factor that limits processing of liquids in apparatus according to the invention. If during processing evaporation occurs, confinement by one of the confining phaseguides may be lifted, potentially leading to incorrect behaviour, e.g. during (selective) recovery after processing. A repetitive pattern of phaseguides of the same stability may be of particular benefit in this regard, as a meniscus that recedes through evaporation thus loses confinement and soon encounters a repetitive phaseguide by which it will be newly confined. This may if necessary occur more than once.

Along similar lines, phaseguides may be repeated to compensate for unintended overflow. This is particularly useful for excess flow phaseguides 22 and phaseguides 31.

There are many different ways of fabricating the above-mentioned screening chamber arrays. Some preferred embodiments of the invention are based on or compatible with standard microtiter plates, including the plate dimensions and inter-well distances, or pitch. Typical well formats are 6, 24, 96, 384, 1536 well plates.

In such an embodiment, wells are contacting inlets, supply conduits or common feeding conduits, while venting conduits may or may not be in contact with a well. In some cases it might be beneficial if only parts of well positions of standard well plates are in use. An example may be that each second row of wells from a 384 well plate addresses a number of inlets or conduits, while the second row is omitted, thus in essence having only 192 active wells.

The well plate dimensions allow use of embodiments of the invention in a standard laboratory automation setup, without large instrument development. An example of this may include pipetting robots that are commonly used in the pharmaceutical and biotech industries.

Such robots might need adjustment in terms of readout, heating and eventual actuation of the volumes or compounds in the volumes.

In addition the robot and/or components of the invention might need adjustments for applying suction or pressure to the wells during filling, metering and/or recovery.

One exemplary way of doing this is by applying a seal between a distal end of a pump, such as a pipette or another dispensing unit, and the well of or connected to the invention.

In another embodiment the structure in accordance with the invention may be connected to a vacuum manifold in order to allow transport of liquid-based substances.

The wells could be manufactured by milling or moulding in one piece of material (plastics, ceramics, glass, other) or by assembling them from sub-components.

The microfluidics parts, including the channels and phaseguides, may be patterned on the in-use underside of the well layer and lain over a bottom layer, either through lamination or bonding.

An alternative is to pattern wells and microfluidic structures in separate plates, followed by bonding. It is also possible to pattern part of the microfluidics volumes, e.g. the phaseguides, in one material; and other parts of the channel, e.g. the channels and chambers, in a second block of material.

Another option is to pattern microfluidic structures in an intermediate layer that is sandwiched in between the top substrate including the wells, and a bottom substrate. The intermediate layer may be e.g. a dry film resist, or a laser cut structure.

The phaseguides may be patterned in this same intermediate material (see Vulto et al. 2010, for an example in dry film resist). Phaseguides may also be patterned as a thin layer, e.g. through photolithography or screen-printing.

For multiple microfluidic channel layers, similar choices could be made. A first layer of microfluidic channels could be structured on the bottom side of the well-plate, overlying an intermediate layer having through-holes in a laminated or bonded construction; and a bottom substrate could include a second channel layer. Alternatively, first and second microfluidic layers may be patterned on the top and bottom of an in-between substrate that also has through holes. This substrate may be sandwiched between the top well-plate and a bottom substrate through a laminating or bonding technique.

There are various ways of providing for venting in the fabricated structures of apparatuses, as described above, in accordance with the invention.

The simplest method is to use an inlet well. However this does not represent the most efficient use of space. Alternatively venting holes may be inserted intermediate inlet holes or wells, passing straight through well-plates to the microfluidic structure layer.

Another embodiment is one in which the well plate is hollow from the inside and venting is effected into this hollow space. Also venting may be done sideways using only the plane of the microfluidic layer itself to define a vent hole. This same approach may also be used on a second plane: a sideways venting approach is used on a higher or lower plane with respect to the microfluidic layer.

In case of venting through the bottom of the plate, an additional capsule may be placed underneath to prevent contamination or accidental spilling of liquids.

Wicking structures can be incorporated in the excess flow volume for absorbing excess flow.

Overall the invention provides considerable versatility in the processing of liquid-based substances.

The listing or discussion of an apparently prior-published document in this specification should not necessarily be taken as an acknowledgement that the document is part of the state of the art or is common general knowledge.

The invention claimed is:

1. An apparatus for processing liquids or liquid-based substances, the apparatus comprising a plurality of volumes, each comprising at least an inlet conduit and at least an outlet conduit, at least two of which volumes are defined at least in part by one or more phaseguides inside the volume and/or in the inlet or outlet conduit connected thereto for controlling aliquoting of one or more liquids or liquid-based substances inside the volume, each volume having an upstream and downstream side with respect to a meniscus movement direction defined during filling of the volume with or emptying of the volume of one or more liquids or liquid-based substances, the apparatus including at least one common upstream-side conduit connected to a plurality of the inlet conduits to supply a fluid via the plurality of inlet conduits to the plurality of the volumes, each of the phaseguides spanning a complete length, width or height of an advancing meniscus and exhibiting a predetermined level of stability and one or more of the phaseguides exhibiting a predetermined different stability compared with the stability of at least one of the other phaseguides whereby to control the preference order in which overflow of the phaseguides occurs during filling and/or emptying of at least one said volume; the said stability being determined by the value and radius of an angle subtended by a formation along a said phaseguide at the downstream side of the phaseguide; wherein the formation is, or comprises at least one of a bend of the downstream-side of the phaseguide, a branch of the downstream-side of the phaseguide, an inlet to the downstream-side of the phaseguide or the intersection of the downstream-side of the phaseguide with a wall.

2. The apparatus of claim 1, wherein the apparatus comprises a plurality of volumes at least two of which are defined at least in part by one or more phaseguides inside the volume for controlling aliquoting of one or more liquids or liquid-based substances inside the volume, each volume having at least two inlets, whereby to permit addition of at least two liquids to at least one said volume containing at least one phaseguide, each volume having an upstream and downstream side with respect to a meniscus movement direction defined during filling of the volume with or emptying of the volume of one or more liquids or liquid-based substances, the apparatus including at least one common upstream-side conduit connected to at least one inlet of the plurality of volumes to supply a liquid or liquid-based substance via the inlet; the apparatus being operative to confine a first liquid or liquid-based substance in a said volume before permitting addition of a second said liquid or liquid-based substance to said volume.

3. The apparatus according to claim 1 or claim 2, wherein one or more of the volumes have at least one phaseguide upstream in or associated with the volume with respect to meniscus advancement.

4. The apparatus according to claim 1 or claim 2, wherein one or more of the volumes have at least one phaseguide downstream in or associated with the volume with respect to meniscus advancement.

5. The apparatus according to claim 1 or claim 2, wherein at least one said volume includes or is associated with an upstream-side phaseguide in or associated with a first said volume that is of lower stability than at least one other downstream-side phaseguide in or associated with at least one second said volume.

6. The apparatus according to claim 1 or claim 2, comprising a common downstream-side conduit for two or more said volumes wherein a first phaseguide at the downstream side of the volume influencing the common downstream-side conduit or a further fluid-containing feature connected thereto and lying furthest from the relatively downstream origin of the common downstream-side conduit, is of lower stability than at least one further phaseguide at the downstream side of a further volume connected to said downstream-side conduit and lying closer than the first downstream-side phaseguide to the relatively downstream origin of the common downstream-side conduit.

7. The apparatus according to claim 6 wherein the common downstream-side conduit includes at least one volume or further fluid-containing structure branched therefrom and having a phaseguide positioned distally from the relatively downstream origin of the common downstream conduit with respect to at least one branched volume that includes at least one upstream-side phaseguide inside the said volume or upstream from it, the distally positioned phaseguide being of lower stability than the said at least one upstream-side phaseguide, such that upon emptying of the volume said first phaseguide is flowed over thereby emptying the conduit and isolating the liquid in said at least one volume.

8. The apparatus according to claim 6 additionally comprising a high-hierarchy common downstream-side conduit that is connected to and of higher hierarchy than the common downstream-side conduit and to one or more further common downstream-side conduits also of lower hierarchy, each further common downstream-side conduit of lower hierarchy being connected to a plurality of volumes; and wherein the high-hierarchy common downstream-side conduit includes a relatively low stability phaseguide that is of higher stability than a phaseguide of lower stability in a branch of lower hierarchy.

9. The apparatus according to claim 1 or claim 2, wherein at least one said volume is internally divided by at least two phaseguides into first, second and third parts, at least one volume part being in contact with a conduit.

10. The apparatus according to claim 9 wherein at least one phaseguide includes a defined location of phaseguide instability at which overflow of the at least one phaseguide initiates in order to establish contact between two liquid-based substances.

11. The apparatus according to claim 10 wherein a downstream-side conduit is connected to the second part of the volume between the two phaseguides and two upstream conduits are connected to the first and third parts of the volume on either side of the two phaseguides, the apparatus being configured to bring two liquids into contact.

12. The apparatus according to claim 11 wherein the location of phaseguide instability lies remote from the downstream conduit in communication with the second volume part.

13. The apparatus of claim 1, wherein a draft angle of a sidewall of each phaseguide to a counter substrate is less than 10°.

14. The apparatus of claim 2, wherein a draft angle of a sidewall of each phaseguide to a counter substrate is less than 10°.

* * * * *